(12) United States Patent
Aqad et al.

(10) Patent No.: US 9,256,125 B2
(45) Date of Patent: Feb. 9, 2016

(54) ACID GENERATORS AND PHOTORESISTS COMPRISING SAME

(71) Applicant: Rohm and Haas Electronic Materials LLC, Marlborough, MA (US)

(72) Inventors: Emad Aqad, Northborough, MA (US); Irvinder Kaur, Westborough, MA (US); Cong Liu, Shrewsbury, MA (US); Cheng-Bai Xu, Southborough, MA (US)

(73) Assignee: Rohm and Haas Electronic Materials, LLC, Marlborough, MA (US)

( * ) Notice: Subject to any disclaimer, the term of this patent is extended or adjusted under 35 U.S.C. 154(b) by 0 days.

(21) Appl. No.: 13/854,078

(22) Filed: Mar. 30, 2013

(65) Prior Publication Data
US 2014/0295347 A1    Oct. 2, 2014

(51) Int. Cl.
| | | |
|---|---|---|
| G03F 7/004 | (2006.01) |
| C07D 319/06 | (2006.01) |
| C07D 317/34 | (2006.01) |
| C07D 317/72 | (2006.01) |
| C07D 319/08 | (2006.01) |
| C07C 309/12 | (2006.01) |
| G03F 7/039 | (2006.01) |

(52) U.S. Cl.
CPC ............ *G03F 7/0045* (2013.01); *C07C 309/12* (2013.01); *C07D 317/34* (2013.01); *C07D 317/72* (2013.01); *C07D 319/06* (2013.01); *C07D 319/08* (2013.01); *G03F 7/0392* (2013.01); *C07C 2103/74* (2013.01); *G03F 7/039* (2013.01)

(58) Field of Classification Search
CPC ..... G03F 7/039; G03F 7/0395; G03F 7/0397; G03F 7/2041; G03F 7/2053; G03F 7/0045; C07C 381/12; C07D 307/32; H01L 21/027
USPC ............... 430/913, 270.1, 914; 549/200, 204, 549/263, 295, 296
See application file for complete search history.

(56) References Cited

U.S. PATENT DOCUMENTS

| | | | | | |
|---|---|---|---|---|---|
| 3,294,743 | A | * | 12/1966 | Mack | 528/116 |
| 3,404,162 | A | * | 10/1968 | Selman | 549/274 |
| 3,523,920 | A | * | 8/1970 | Schultz | 524/425 |
| 3,952,016 | A | * | 4/1976 | Barillo et al. | 549/274 |
| 3,989,637 | A | * | 11/1976 | Hogue et al. | 252/180 |
| 4,070,375 | A | * | 1/1978 | Suzuki | 549/274 |
| 4,142,057 | A | * | 2/1979 | Suzuki | 562/525 |
| 4,166,821 | A | * | 9/1979 | Suzuki | 549/274 |
| 4,348,322 | A | * | 9/1982 | Edwards et al. | 549/296 |
| 4,366,270 | A | * | 12/1982 | Ruter | 523/307 |
| 4,418,087 | A | * | 11/1983 | Pittet et al. | 426/536 |
| 4,824,970 | A | * | 4/1989 | Castaldi et al. | 549/296 |
| 4,990,629 | A | * | 2/1991 | Souma | 549/267 |
| 5,061,793 | A | * | 10/1991 | Grindey et al. | 536/27.14 |
| 5,106,995 | A | * | 4/1992 | Plotkin | 549/273 |
| 5,235,031 | A | * | 8/1993 | Drysdale et al. | 528/354 |
| 5,279,921 | A | * | 1/1994 | Onishi et al. | 430/270.1 |
| 5,424,136 | A | * | 6/1995 | Hermes | 428/524 |
| 5,488,095 | A | * | 1/1996 | Boeckh et al. | 510/479 |
| 5,639,903 | A | * | 6/1997 | Takahashi et al. | 560/15 |
| 5,951,997 | A | * | 9/1999 | Bezwada et al. | 424/426 |
| 6,346,599 | B1 | * | 2/2002 | Goldberg et al. | 528/354 |
| 6,602,647 | B2 | * | 8/2003 | Iwasa et al. | 430/270.1 |
| 7,141,351 | B2 | * | 11/2006 | Watanabe et al. | 430/270.1 |
| 7,316,884 | B2 | * | 1/2008 | Ansai et al. | 430/270.1 |
| 7,459,260 | B2 | | 12/2008 | Chandhok et al. | |
| 7,746,679 | B2 | * | 6/2010 | Gronlund | 365/49.17 |
| 8,263,788 | B2 | * | 9/2012 | Brandenburg et al. | 549/59 |
| 8,318,403 | B2 | * | 11/2012 | Ichikawa et al. | 430/270.1 |
| 8,354,217 | B2 | * | 1/2013 | Ichikawa et al. | 430/270.1 |
| 8,367,298 | B2 | * | 2/2013 | Ichikawa et al. | 430/270.1 |
| 8,404,427 | B2 | * | 3/2013 | Wada et al. | 430/270.1 |
| 9,067,909 | B2 | | 6/2015 | Kaur et al. | |
| 9,110,369 | B2 | | 8/2015 | Aqad et al. | |
| 2004/0248031 | A1 | | 12/2004 | Ansai et al. | |
| 2006/0047129 | A1 | * | 3/2006 | Nugent et al. | 549/296 |
| 2006/0141383 | A1 | * | 6/2006 | Miyamatsu et al. | 430/270.1 |
| 2007/0224540 | A1 | | 9/2007 | Kamimura et al. | |
| 2010/0099042 | A1 | * | 4/2010 | Ohashi et al. | 430/270.1 |
| 2010/0239978 | A1 | * | 9/2010 | Wada et al. | 430/270.1 |
| 2010/0248135 | A1 | * | 9/2010 | Masuyama et al. | 430/270.1 |
| 2010/0304294 | A1 | * | 12/2010 | Ichikawa et al. | 430/270.1 |
| 2011/0014568 | A1 | | 1/2011 | Ichikawa et al. | |
| 2011/0189607 | A1 | * | 8/2011 | Ohashi et al. | 430/270.1 |
| 2011/0282004 | A1 | * | 11/2011 | Tanaka | 525/55 |
| 2012/0065291 | A1 | | 3/2012 | Matsumura et al. | |
| 2012/0107744 | A1 | * | 5/2012 | Utsumi et al. | 430/283.1 |
| 2012/0156612 | A1 | * | 6/2012 | Asano et al. | 430/270.1 |
| 2013/0183624 | A1 | * | 7/2013 | Maruyama | 430/311 |
| 2014/0356785 | A1 | | 12/2014 | Williams, III et al. | |
| 2015/0064620 | A1 | | 3/2015 | Kaur et al. | |

FOREIGN PATENT DOCUMENTS

| | | | |
|---|---|---|---|
| EP | 1906241 A1 | | 4/2008 |
| JP | 62205075 A | * | 9/1987 |
| JP | 06025591 A | * | 2/1994 |
| JP | 2008007421 A | * | 1/2008 |
| JP | 2011-201866 A | | 10/2011 |
| JP | 2011201866 A | * | 10/2011 |

OTHER PUBLICATIONS

Search Report for Taiwan Patent Application No. 103111924 Dec. 16, 2014.

* cited by examiner

*Primary Examiner* — Amanda C Walke
(74) *Attorney, Agent, or Firm* — Mintz Levin Cohn Ferris Glovsky and Popeo, P.C.; Peter F. Corless

(57) ABSTRACT

Acid generator compounds are provided that comprise an oxo-1,3-dioxolane moiety and/or an oxo-1,3-dioxane moiety. The acid generators are particularly useful as a photoresist composition component.

21 Claims, No Drawings

ACID GENERATORS AND PHOTORESISTS COMPRISING SAME

FIELD

The present invention relates to new acid generators that comprise an oxo-dioxolan and/or oxo-dioxane moiety.

INTRODUCTION

Photoresists are photosensitive films for transfer of images to a substrate. They form negative or positive images. After coating a photoresist on a substrate, the coating is exposed through a patterned photomask to a source of activating energy such as ultraviolet light to form a latent image in the photoresist coating. The photomask has areas opaque and transparent to activating radiation that define an image desired to be transferred to the underlying substrate. A relief image is provided by development of the latent image pattern in the resist coating.

Known photoresists can provide features having resolution and dimension sufficient for many existing commercial applications. However for many other applications, the need exists for new photoresists that can provide highly resolved images of submicron dimension.

Various attempts have been made to alter the make-up of photoresist compositions to improve performance of functional properties. Among other things, a variety of photoactive compounds have been reported for use in photoresist compositions. See US 20070224540 and EP 1906241. See also US 2012/0065291. Short-wavelength imaging also has been utilized, such as 193 nm. Extreme ultraviolet (EUV) and e-beam imaging technologies also have been employed. See U.S. Pat. No. 7,459,260. EUV utilizes short wavelength radiation, typically between 1 nm to 40 nm, with 13.5 nm radiation often employed.

EUV photoresist development continues to be a challenging issue for EUV Lithography (EUVL) technology implementation. Required are development of materials that can provided highly resolved fine features, including low linewidth roughness (LWR), and sufficient sensitivity to afford wafer throughput.

SUMMARY

We have now discovered new acid generators and photoresist compositions that comprise one or more of such acid generators.

Acid generators are provided that comprise an oxo-dioxolan moiety (such as an oxo-1,3-dioxolan group) and/or an oxo-dioxane (such as an oxo-1,3-dioxane group) moiety.

Particularly preferred acid generators may comprise a moiety of the following Formulae I or II:

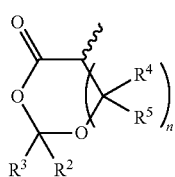

(I)

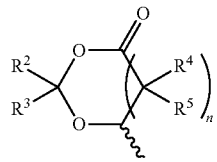

(II)

wherein in each of Formulae I and II:

$R^2$, $R^3$, $R^4$ and $R^5$ are each independently hydrogen or a non-hydrogen substituent such as optionally substituted alkyl, optionally substituted heteroalkyl, optionally substituted alicyclic, optionally substituted heteroalicyclic, optionally substituted carbocyclic aryl or optionally substituted heteroaromatic, preferably where at least one, or both, of $R^2$ and $R^3$ is a non-hydrogen substituent;

$R^2$ and $R^3$ optionally may be taken together to form a ring such as optionally substituted $C_{3-30}$ alicyclic which optionally may have 1, 2, or 3 N, O or S ring members;

$R^4$ and $R^5$ optionally may be taken together to form a ring such as optionally substituted $C_{3-30}$ alicyclic which optionally may have 1, 2, or 3 N, O or S ring members; and the waved line represents a covalent linkage connecting the depicted moiety to the larger acid generator material;

$R^4$ and/or $R^5$ optionally may be taken together with the covalent linkage to form a ring such as optionally substituted $C_{3-30}$ alicyclic which optionally may have 1, 2, or 3 N, O or S ring members; and n is 0 or 1. In certain preferred compounds $R^2$, $R^3$, $R^4$ and $R^5$ are not taken together to form a ring. In other preferred compounds, at least one of 1) $R^2$ and $R^3$ and 2) $R^4$ and $R^5$ are taken together to form a ring.

In certain particularly preferred aspects, in Formulae I and II, n is 0 (i.e. the depicted structure is a 5-membered ring), such as oxo-1,3-dioxolan groups of the Formula III:

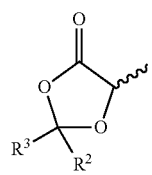

III wherein $R^2$ and $R^3$ are each independently hydrogen or non-hydrogen substituent, and $R^2$ and $R^3$ may be optionally taken together to form a ring such as optionally substituted $C_{3-30}$ alicyclic which optionally may have 1, 2, or 3 N, O or S ring members; and the waved line represents a covalent linkage to the photoacid generator. In Formula III, preferably at least one, or both, of $R^2$ and $R^3$ is a non-hydrogen substituent.

In certain preferred aspects, the present acid generators are onium compounds, such as iodonium or sulfonium materials, with sulfonium acid generators being generally preferred. Particularly preferred acid generators include those of the following Formula IV:

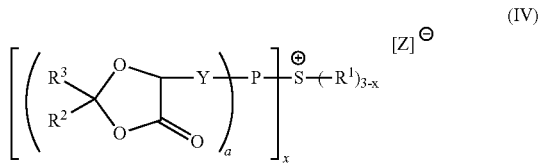

(IV)

wherein:

x is 1, 2 or 3;

a is a positive integer of from 1 to 12;

$R^2$ and $R^3$ are each independently hydrogen, optionally substituted alkyl, optionally substituted heteroalkyl, optionally substituted alicyclic; optionally substituted heteroalicyclic; optionally substituted carbocyclic aryl; or optionally substituted heteroaromatic, or $R^2$ and $R^3$ may be taken together to form an aromatic or non-aromatic cyclic group such as optionally substituted $C_{3-30}$alicyclic which optionally may have 1, 2, or 3 N, O or S ring members, preferably at least one, or both, of $R^2$ and $R^3$ not being hydrogen;

Y is a covalent bond or a linker group;

P is optionally substituted alkyl, optionally substituted heteroalkyl, optionally substituted alicyclic, optionally substituted heteroalicyclic, optionally substituted carbocyclic aryl, optionally substituted heteroaromatic;

each $R^1$ is independently optionally substituted alkyl, optionally substituted heteroalkyl; optionally substituted alicyclic; optionally substituted heteroalicyclic; optionally substituted optionally substituted carbocyclic aryl; or optionally substituted heteroaromatic aryl;

when x is 1, two $R^1$ groups optionally may be taken together with the depicted $S^+$ to form an optionally substituted ring structure such as optionally substituted $C_{3-30}$alicyclic which optionally may have 1, 2, or 3 N, O or S ring members in addition to the depicted $S^+$; and Z is a counter anion.

In preferred aspects, an acid generator comprises an oxo-dioxane moiety, such as a group of the above Formula I or II, where n is 1.

Preferred acid generators and photoresists of the invention are particularly useful for short-wavelength imaging, such as 193 nm and EUV imaging.

In preferred aspects, photoresist compositions are provided comprising (i) a polymer; and (ii) an acid generator as disclosed herein.

In preferred aspects, the acid generators are acid-labile and react in the presence of acid during lithographic processing (exposure, post-exposure bake) of a photoresist coating layer containing the acid generator. In particular, in preferred materials, the oxo-dioxolan moiety, including a group of Formula I or II, and/or oxo-dioxane moiety may react during lithographic processing of a photoresist comprising the acid generator to provide a bound hydroxyl acetic acid group (—(CHOH)COOH).

Preferred photoresists of the invention may comprise an imaging-effective amount of two or more acid generator compounds as disclosed herein and a suitable polymer component.

Methods are also provided for forming relief images of photoresist compositions of the invention (including patterned lines with sub sub-50 nm or sub-20 nm dimensions). Substrates such as a microelectronic wafer also are provided having coated thereon a photoresist composition of the invention.

DETAILED DESCRIPTION

As referred to herein, acid generators can produce an acid when exposed to activating radiation, such as EUV radiation, e-beam radiation, 193 nm wavelength radiation or other radiation sources. Acid generator compounds as referred to herein also may be referred to as photoacid generator compounds.

Acid Generators

As discussed above, in preferred aspects, ionic photoacid generators that comprise an oxo-1,3-dioxolan moiety are provided, including sulfonium acid generators, such as compounds of the following Formula V:

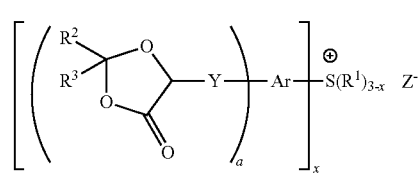

V wherein in Formula V:

a is an integer from 1 to 12;

x is an integer from 1 to 3,

Y is a linker;

Ar is an optionally substituted $C_5$ or greater monocyclic, polycyclic, or fused polycyclic cycloalkyl; or an optionally substituted $C_5$ or greater monocyclic, polycyclic, or fused polycyclic aryl group, wherein the cycloalkyl or aryl is a carbocycle (e.g. phenyl, naphthyl, anthracenyl) or comprises a heteroatom comprising O, S, N, F, or a combination comprising at least one of the foregoing, each $R^1$ is independently optionally substituted carbocyclic aryl; optionally substituted heteroaryl; optionally substituted alkyl preferably having 1 to 20 carbon atoms, a $C_{3-40}$ cycloalkyl, wherein when x is 1, two groups $R^1$ may be optionally taken together to form a ring structure, $R^2$ and $R^3$ independently are hydrogen or a non-hydrogen substituent such as optionally substituted alkyl preferably having 1 to 20 carbon atoms, optionally substituted heteroalkyl preferably having 1 to 20 carbon atoms and 1, 2 or 3 N, O or S atoms, optionally substituted alicyclic preferably having 3 to 20 carbon atoms, optionally substituted heteroalicyclic, optionally substituted carbocyclic aryl or optionally substituted heteroaromatic, and preferably one or both of $R^2$ and $R^3$ is a non-hydrogen substituent;

$Z^-$ is a non-nucleophilic anion such as carboxylate, sulfate, sulfonate, sulfamate, or the anion of a sulfonamide.

In the above Formula V, Y suitably can be a single bond, optionally substituted alkylene group, O, S, NR (where R is a non-hydrogen substituent such as optionally alkyl). Y linker groups also may comprise various hetero groups such as ether, ester, amide, carbonate, sulfonate, sulfone, or sulfonamide, e.g. $CH_2(C{=}O){-}O{-}$, $CH_2(C{=}O){-}OCH_2CH_2{-}$, $CH_2(C{=}O){-}OCH_2CH_2O{-}$, $CH_2(C{=}O){-}OCH_2{-}$, $CH_2(C{=}O){-}OCH_2O{-}$, $-O-$, $-S-$, $-O-C(=O)-$, $-C(=O)-O-$, $-O-C(=O)-O-$, $-OCH_2-(C{=}O)O-$ or $-OCH_2C(=O)-$.

In another aspect, preferred are ionic acid generators that comprise an oxo-1,3-dioxane moiety, including sulfonium-acid generators, such as compounds of the following Formulae VI and VII:

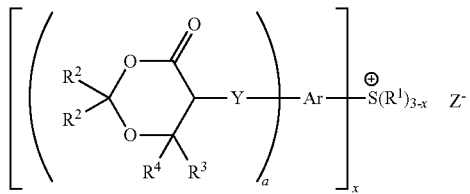

VI

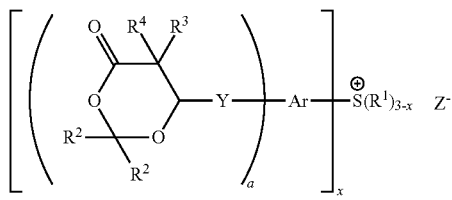

VII wherein $R^2$, $R^3$, $R^4$, $R^5$, Y, Ar, $R^1$, x and a are as described above in Formula V above, or $R^4$ and/or $R^5$ in structures VI and VII can optionally covalently attach to Y to form a ring such as exemplified by the following structures C1 and C2:

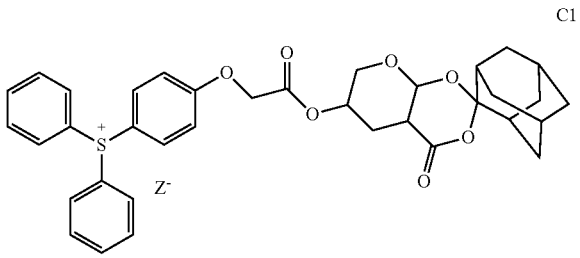

C1

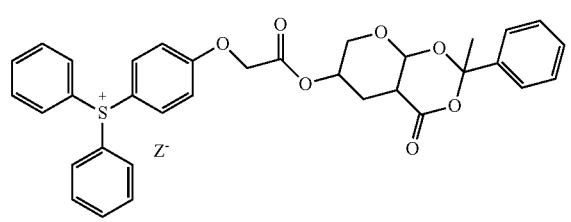

C2

Specifically preferred cations of ionic acid generators acid generator include the following sulfonium cations A1 through A12:

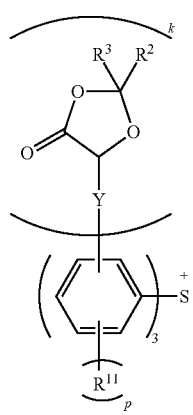

A1

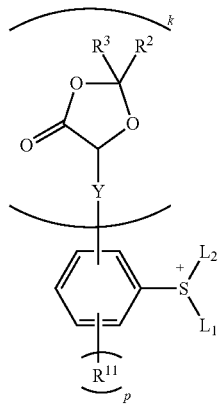

A2

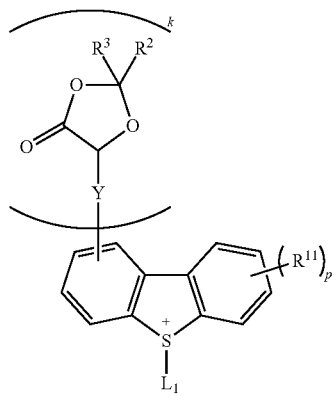

A3

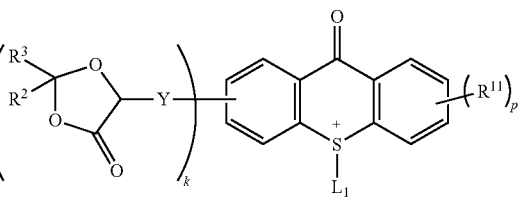

A4

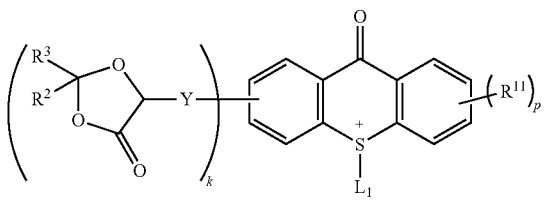

A5

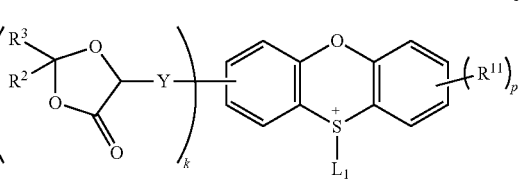

A6

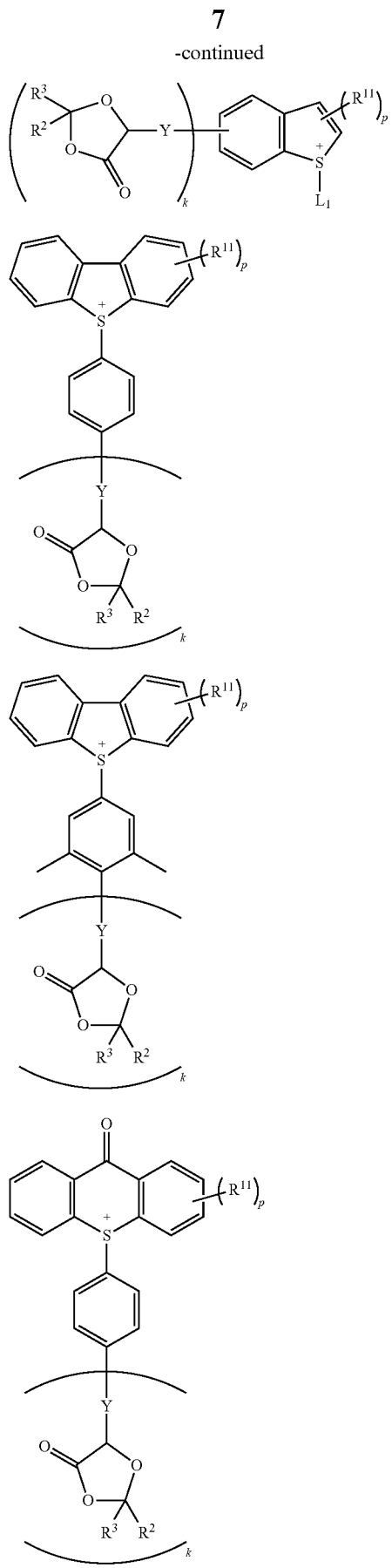
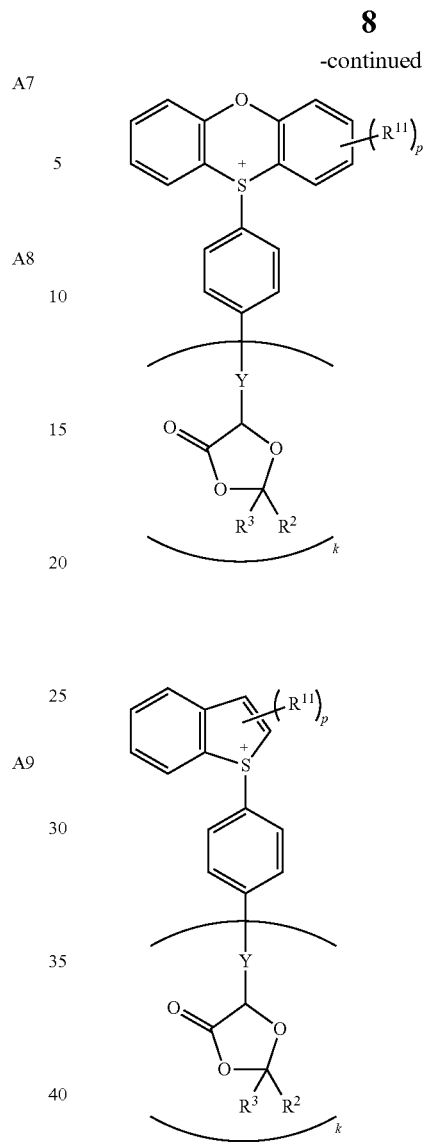

wherein in those formulae A1 through A12 each $L_1$ and $L_2$ are independently optionally substituted carbocyclic aryl, optionally substituted heteroaryl, optionally substituted alkyl (including cycloalkyl), wherein the two $L_1$ and $L_2$ may be optionally taken together to form a ring structure, $R^2$ and $R^3$ are the same as defined in Formula V above.

$R^{11}$ is a non-hydrogen substituent; and p is an integer from 0 to 5.

As referred to herein, an oxo-1,3-dioxalan group includes groups that can produce both carboxylic acid and hydroxyl moieties, such as hydroxyl acetic acid group, upon reaction with acid as shown in the following scheme:

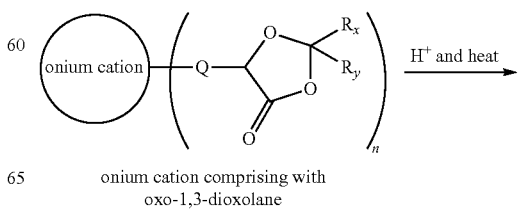

onium cation comprising with oxo-1,3-dioxolane

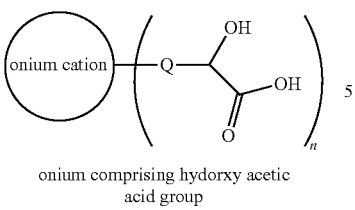

onium comprising hydorxy acetic acid group

Specifically preferred oxo-1,3-dioxalan groups include the following:

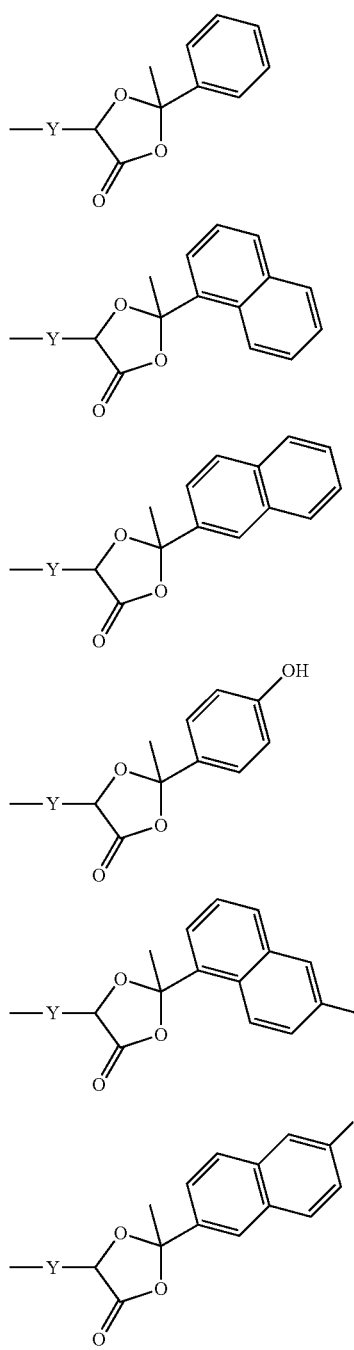

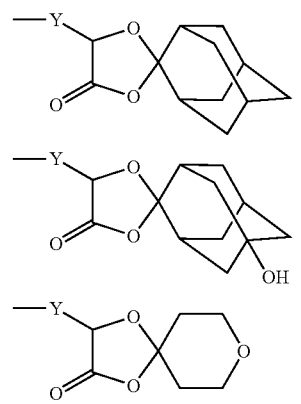

Specifically preferred oxo-dioxane groups include the following:

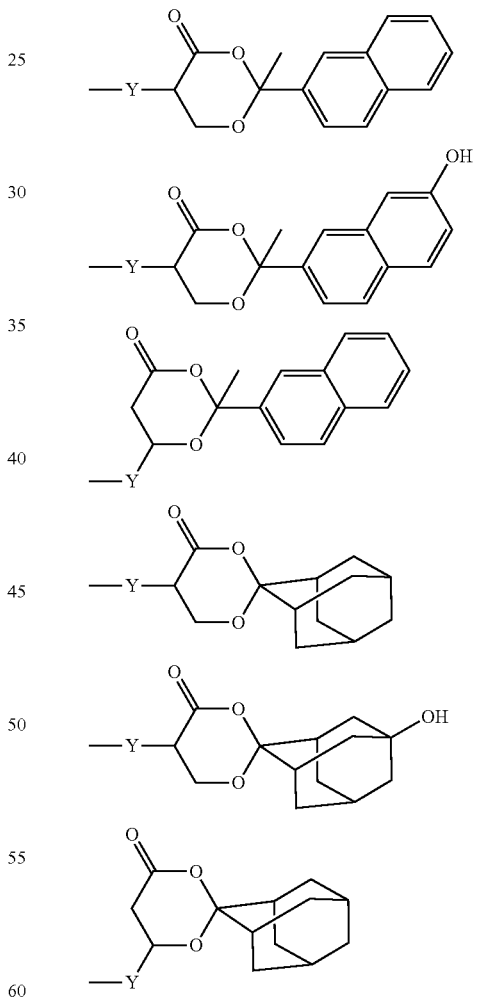

wherein in those structures, Y is a linker group as specified in Formula V above.

Suitable sulfonium cations include those where the photo-acid-labile leaving group comprises an alicyclic or aromatic leaving, such as the following:

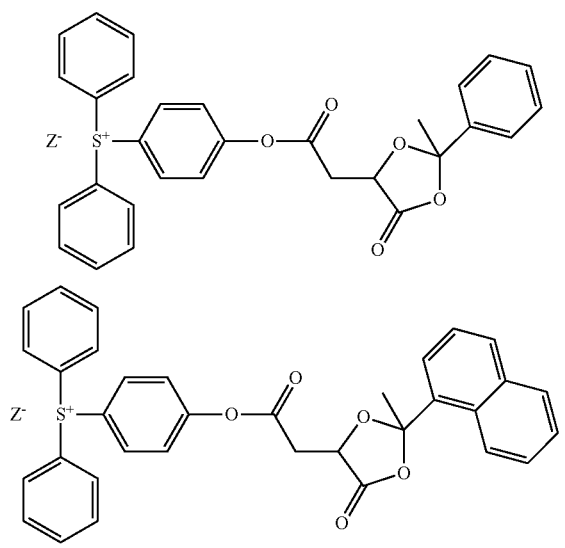
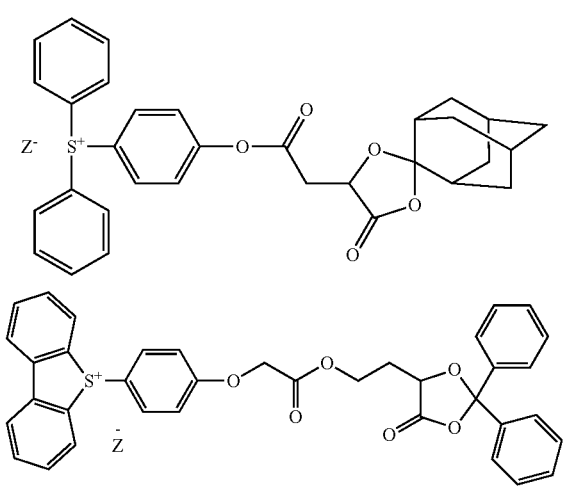
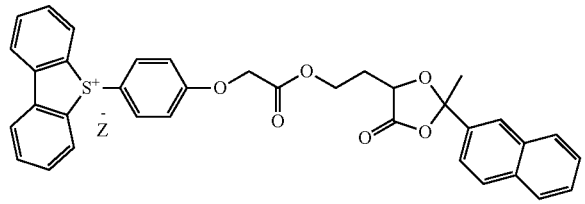
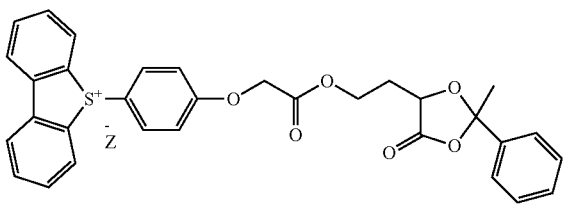
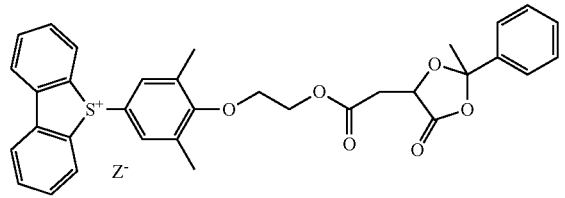
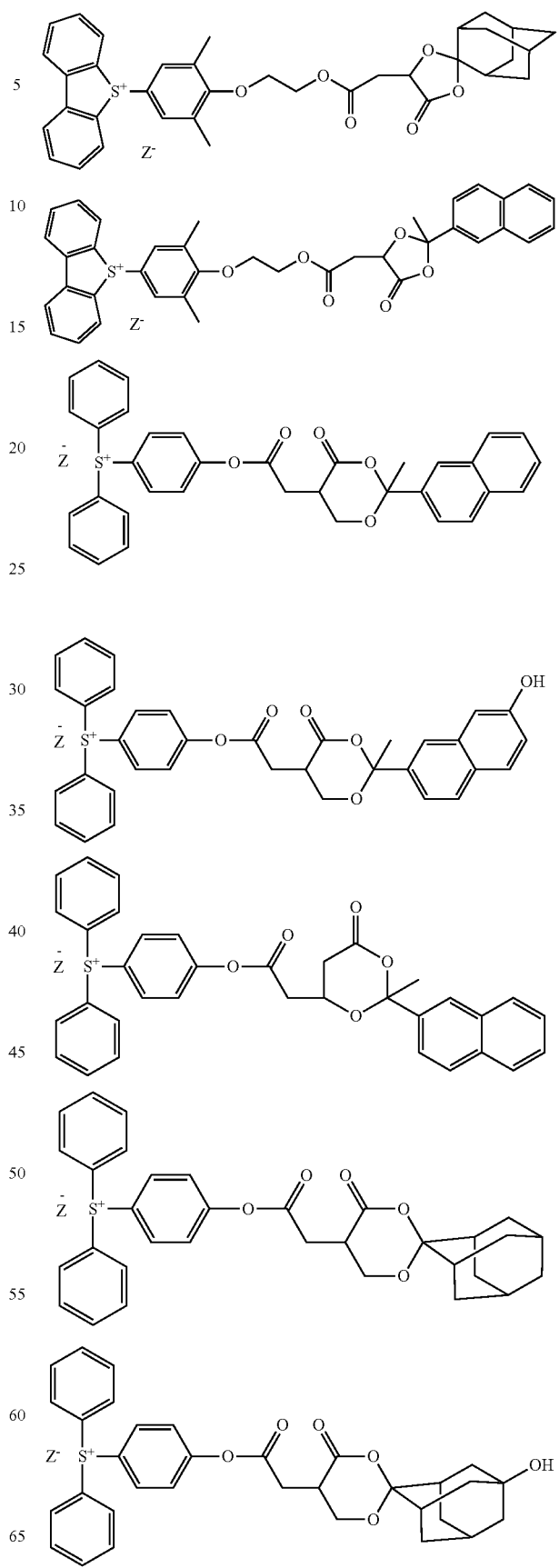

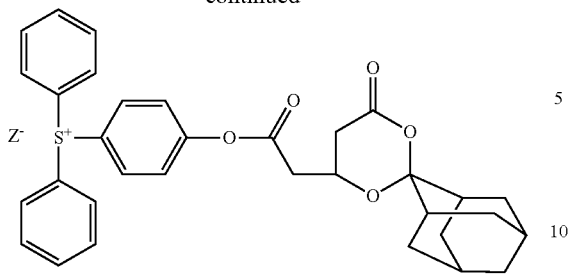

wherein in those structures Z is an anion, preferably a non-nucleophilic anion.

Preferred anion components (Z in the above formulae) of ionic acid generators of the invention include those where wherein the anion charge resides with a sulfonate group, a carboxylate group, a carbon atom, nitrogen atom or boron atom. Exemplary Z groups may comprises optionally substituted alkylsulfonate and optionally substituted carbocyclic arylsulfonate.

Preferred anion components (Z in the above formulae) of ionic acid generators of the invention include those of the following formula:

wherein A is a substituted or unsubstituted, monocyclic, polycyclic, or fused polycyclic $C_3$ or greater aliphatic or aromatic groups optionally comprising O, S, N, F, or a combination comprising at least one of the foregoing, or a $C_3$ or greater aliphatic or cycloaliphatic group containing a polymerizable double or triple bond. Preferred groups A include polycyclic aliphatic groups such as adamantyl groups, norbornenyl groups, and cycloalkylenyl groups substituted with hydroxy, ester, lactone, acetyl, ketyl, or combinations of these groups.

$R^4$ is H, a single bond, or a substituted or unsubstituted $C_{1-30}$ alkyl group, wherein when $R^4$ is a single bond, $R^4$ is covalently bonded to a carbon atom of A;

each $R^5$ is independently H, F, or $C_{1-4}$ fluoroalkyl, wherein at least one $R^5$ is not hydrogen;

$L^1$ is a linking group comprising e.g. an —O—, —S—, —C(=O)—, carbonate, carboxylate, sulfonate, sulfate, or a sulfonamide group;

m1 is an integer of greater than or equal to 0, preferably 0 to 10 or 1 to 5; and n2 is an integer of greater than or equal to 0, preferably 1 to 10 or 1 to 5.

Exemplary anion components (Z in the above formulae) of ionic acid generators of the invention include the following:

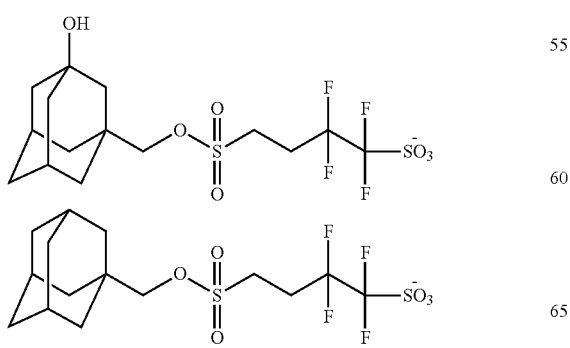

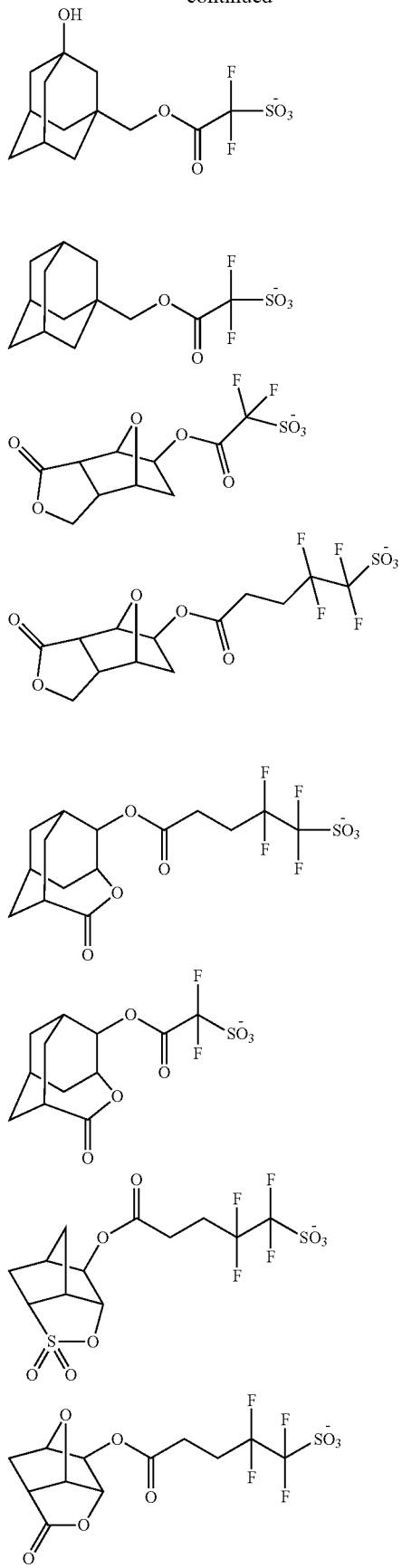

-continued
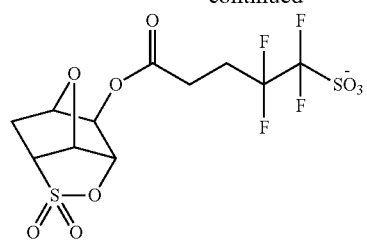
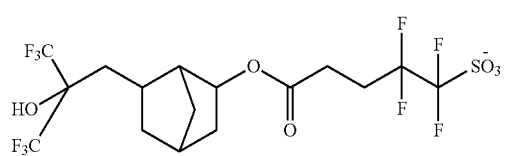
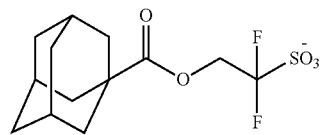
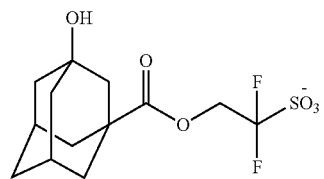
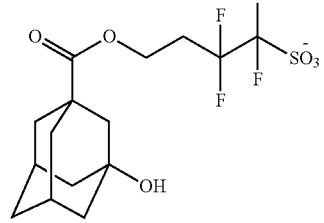
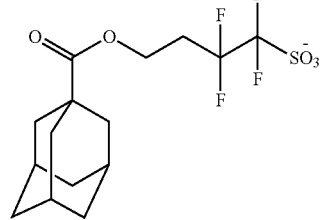
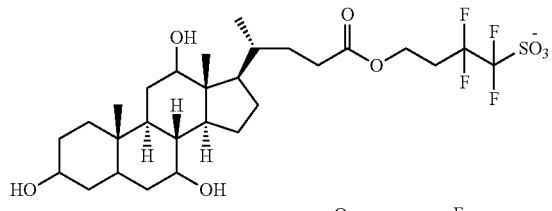
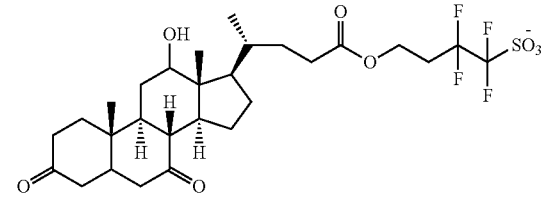
-continued
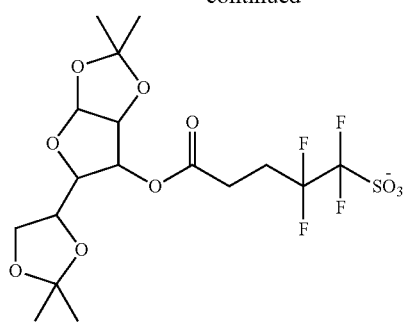
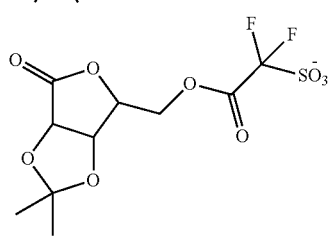
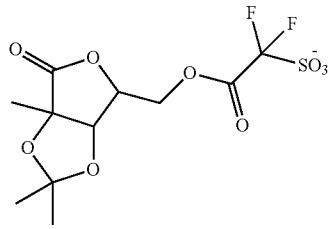
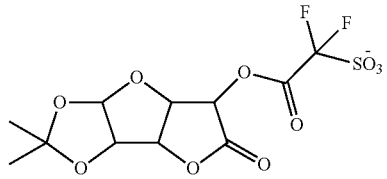
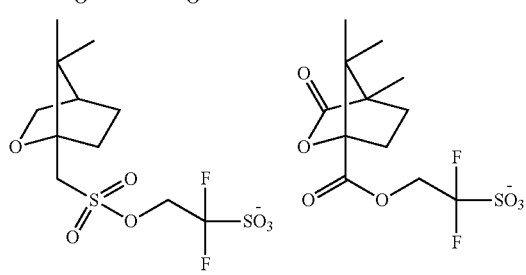
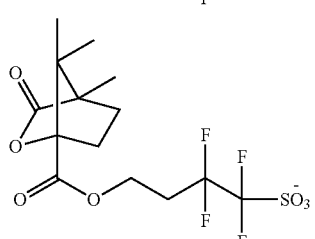
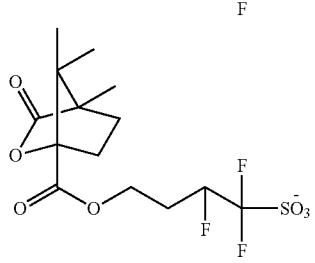

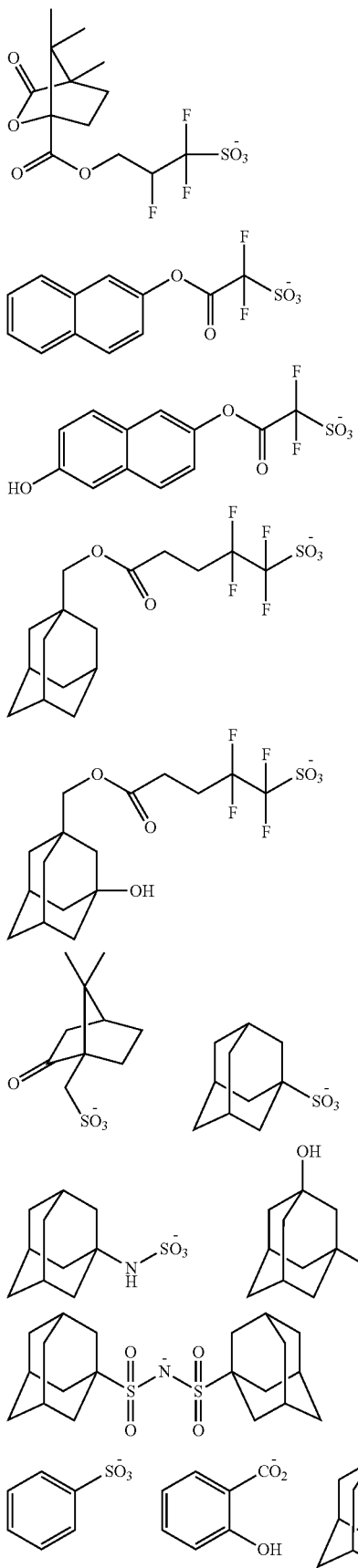

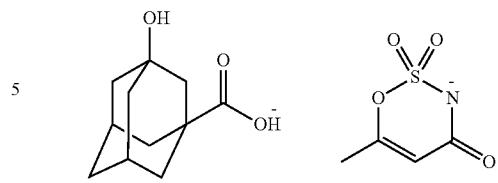

As mentioned above, acid generators of the invention may be covalently bound to a larger polymer. For an ionic acid generator, suitably either cation or anion components are covalently linked to a larger polymer, or both cation and anion components are covalently bound to the polymer.

For instance, the anion component may comprise a polymerizable group (such as acrylate, methacrylate, vinyl ether) which can be reacted with a pre-formed polymer, or other monomers, to provide the polymer-bound acid generator. Exemplary polymerizable anion components include the following structures:

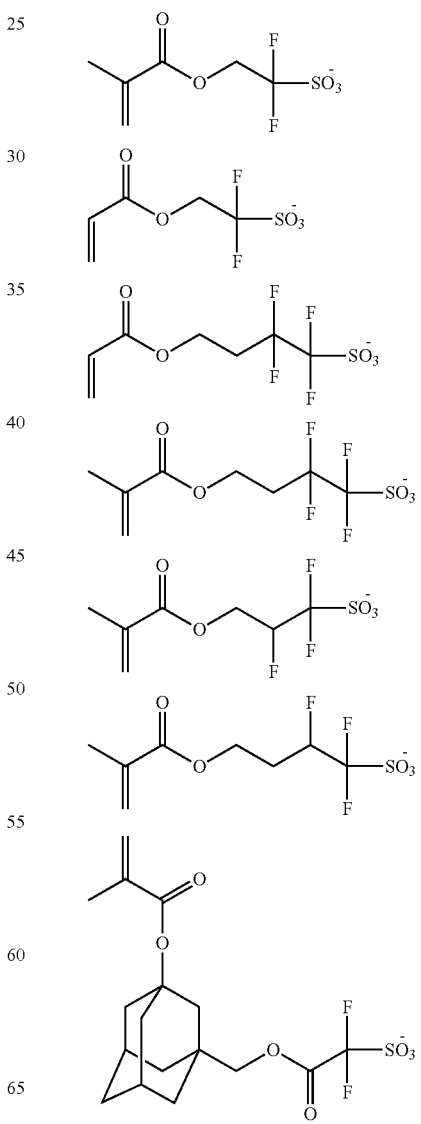

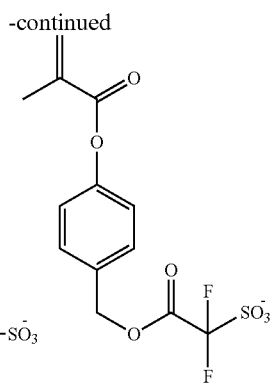

As discussed above, the present acid generator may be acid-labile and undergo a bond-breaking reaction during lithographic processing of a photoresist comprising the acid generator. As discussed above, an acid generator oxo-1,3-dioxolan moiety or oxo-1,3-dioxane moiety itself may be photoacid-labile and react under lithographic processing of a photoresist comprising the acid generator. An acid generator also may comprise other substituents that are photoacid-labile. As referred to herein, acid-labile moieties or groups (including acid-labile esters and acetals) undergo reaction in the presence of generated acid (from an acid generator compound in a resist) during typical lithographic processing, including any post-radiation exposure thermal exposure. Acid-labile groups as referred to herein also may be referred to as photoacid-labile groups.

For acid generators that comprise acid-labile group(s) in addition to or other than an oxo-diolan or oxo-dioxane, suitable acid-labile groups may be a variety of moieties, including acid-labile esters and acetals such as optionally substituted ethylcyclopentyl ester, methyladamantyl ester, ethyl adamantyl ester, t-butylester, phenyl ester, naphthyl ester and others. Suitable acid-labile groups of acid generators also may include groups of the following formula (VIII) and ester photoacid-labile groups of the following formula IX:

—O(CXY)$_n$R$^3$    (VIII)

wherein in Formula (VIII) X and Y are independently hydrogen or a non-hydrogen substituent such as halogen (F, Cl, Br, I), C$_{1-10}$alkyl, C$_{1-10}$alkoxy; R$^3$ is a non-hydrogen substituent that provides an acid-labile moiety such as a carbamate, an acid-labile ester or acetal group; and n is a positive integer such as any of 1 through 20, more typically n is any of 1-10 or 1-4. Exemplary preferred R$^3$ groups include t-butyl, or more preferably a further ester linkage such as where R$^3$ is —(CH$_2$)n(C=O)O-ALG, where n is an integer of from 1 to 12, preferably n is 1, 2, 3 or 4, and ALG is a group (e.g. that provides a quaternary carbon linked to the ester) that results in an acid labile moiety, such as t-butyl or a ring system with linking quaternary carbon such as 1-ethylcyclopentyl or methyladamantyl;

—(C=O)OR$^3$    (IX)

wherein in Formula (IX) R$^3$ is a non-hydrogen substituent that provides an acid-labile moiety such as a carbamate, an acid-labile ester or acetal group. For instance, exemplary preferred R$^3$ groups include t-butyl, or more preferably a further ester linkage such as where R$^3$ is —(CH$_2$)n(C=O)O-ALG, where n is an integer of from 1 to 12, preferably n is 1, 2, 3 or 4, and ALG is a group (e.g. that provides a quaternary carbon linked to the ester) that results in an acid labile moiety, such as t-butyl or a ring system with linking quaternary carbon such as 1-ethylcyclopentyl or methyladamantyl.

In certain aspects, an acid generator of the invention will not contain any acid-labile groups other than an oxo-1,3-dioxolan moiety and/or oxo-1,3-dioxane moiety.

In the above formulae, suitable non-hydrogen substituents may be e.g. non-hydrogen substituent such as halo (F, Cl, Br or I); cynano, nitro, hydroxy, optionally substituted alkyl such as optionally substituted C$_{1-20}$alkyl preferably optionally substituted C$_{1-10}$alkyl (which can includes optionally substituted alicyclic which may preferably have 3 to 20 carbons), optionally substituted heteroalkyl preferably having 1 to 20 carbon atoms and 1, 2 or 3 N, O or S atoms, which may include e.g. optionally substituted alkoxy such as optionally substituted C$_{1-20}$alkoxy, optionally substituted alkylthio preferably having 1 to about 20 carbon atoms, optionally substituted alkylsulfinyl preferably 1 to about 20 carbon atoms, optionally substituted alkylsulfonyl preferably having 1 to about 20 carbon atoms; optionally substituted alkenyl or alkynyl preferably having 2 to about 20 carbon atoms such as such as allyl; optionally substituted ketones preferably having 1 to about 20 carbon atoms; optionally substituted carboxy preferably have 1 to about 20 carbon atoms (which includes groups such as —COOR' where R' is H or C$_{1-8}$alkyl, including esters that are substantially non-reactive with photoacid); optionally substituted alkaryl such as optionally substituted benzyl, optionally substituted carbocyclic aryl such as optionally substituted phenyl, naphthyl, acenaphthyl, or optionally substituted heteroalicyclic or optionally substituted heteroaromatic or heteroaryl group such as pyridyl, furanyl, pyrrole, thiophene, furan, imidazole, pyrazole, oxazole, isoxazole, thiazole, isothiazole, triazole, furanzan, oxadiazole, thiadiazole, dithiazole, terazole, pyran, thiopyran, diazine, oxazine, thiazine, dioxine, dithine, and triazine and polyaromatic groups containing one or more of such moieties.

Preferred acid generators of the invention may comprise one or more electron withdrawing moieties, which suitably may be e.g. halogen such as Cl, Br or F with F being preferred, C$_{1-20}$haloalkyl with fluoroalkyl being preferred including perfluoralkyl; cyano; nitro; C$_{1-20}$alkylsulfonyl, —COOH; and >C=O. For ionic acid generators, one or more electron withdrawing substituents may be present on either cation or anion components.

As discussed, various moieties of acid generators and other materials may be optionally substituted. A "substituted" substituent may be substituted at one or more available positions, typically 1, 2, or 3 positions by one or more suitable groups such as e.g. halogen (particularly F, Cl or Br); cyano; nitro; C$_{1-8}$ alkyl; C$_{1-8}$ alkoxy; C$_{1-8}$ alkylthio; C$_{1-8}$ alkylsulfonyl; C$_{2-8}$ alkenyl; C$_{2-8}$ alkynyl; hydroxyl; nitro; alkanoyl such as a C$_{1-6}$ alkanoyl e.g. acyl, haloalkyl particularly C$_{1-8}$ haloalkyl such as CF$_3$; —CONHR, —CONRR' where R and R' are optionally substituted C$_{1-8}$alkyl; —COOH, COC, >C=O; and the like.

Acid generators of the invention can be readily prepared. Exemplary preferred syntheses are set forth in the examples which follow. For instance, for preparation of an oxo-dioxolan, a malic acid compound may be reacted with a keto compound and then further functionalized by reaction with an ionic compound (e.g. sulfonium or iodonium salt). The resulting acid generator may be suitably anion exchanged if desired to provide an preferred anion component. Oxo-dioxane compounds may be similarly prepared, e.g. by reacting a hydroxyglutaric acid compound with a keto compound and then further functionalized by reaction with an ionic compound (e.g. sulfonium or iodonium salt). An anion-exchange reaction can follow if desired.

Photoresist Compositions

As discussed above, acid generators as disclosed herein are useful as the radiation sensitive component in photoresist compositions, including both positive-acting and negative-acting chemically amplified resist compositions.

Photoresists of the invention typically comprise a polymer and one or more acid generators as disclosed herein. Photoresists may comprise additional photoacid generators, i.e. a resist may comprise a blend of multiple photoacid generators including 1) one or more acid generators comprising an oxo-dioxolan and/or oxo-dioxane moiety and 2) one or more distinct photoacid generators which do not comprise an oxo-dioxolan and/or oxo-dioxane moiety. Preferably the resist polymer has functional groups that impart alkaline aqueous developability to the resist composition. For example, preferred are polymers that comprise polar functional groups such as hydroxyl or carboxylate, or acid-labile groups that can liberate such polar moieties upon lithographic processing. Preferably the polymer is used in a resist composition in an amount sufficient to render the resist developable with an aqueous alkaline solution.

Acid generators are also suitably used with polymers that comprise repeat units containing aromatic groups, such as optionally substituted phenyl including phenol, optionally substituted naphthyl, and optionally substituted anthracene. Optionally substituted phenyl (including phenol) containing polymers are particularly suitable for many resist systems, including those imaged with EUV and e-beam radiation. For positive-acting resists, the polymer also preferably contains one or more repeat units that comprise acid-labile groups. For example, in the case of polymers containing optionally substituted phenyl or other aromatic groups, a polymer may comprise repeat units that contain one or more acid-labile moieties such as a polymer that is formed by polymerization of monomers of an acrylate or methacrylate compound with acid-labile ester (e.g. t-butyl acrylate or t-butyl methacrylate). Such monomers may be copolymerized with one or more other monomers that comprise aromatic group(s) such as optionally phenyl, e.g. a styrene or vinyl phenol monomer.

Preferred monomers used for the formation of such polymers include: an acid-deprotectable monomer having the following formula (V), a lactone-containing monomer of the following formula (VI), a base-soluble monomer of the following formula (VII) for adjusting dissolution rate in alkaline developer, and a photoacid-generating monomer of the following formula (VIII), or a combination comprising at least one of the foregoing monomers:

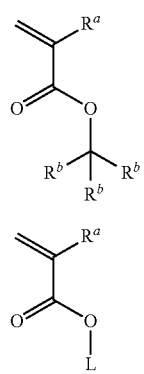

(V)

(VI)

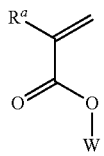

(VII)

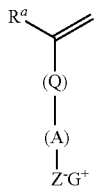

(VIII)

wherein each $R^a$ is independently H, F, —CN, $C_{1-10}$ alkyl, or $C_{1-10}$ fluoroalkyl. In the acid-deprotectable monomer of formula (V), $R^b$ is independently $C_{1-20}$ alkyl, $C_{3-20}$ cycloalkyl, $C_{6-20}$ aryl, or $C_{7-20}$ aralkyl, and each $R^b$ is separate or at least one $R^b$ is bonded to an adjacent $R^b$ to form a cyclic structure. In lactone-containing monomer of formula (VI), L is a monocyclic, polycyclic, or fused polycyclic $C_{4-20}$ lactone-containing group. In the base solubilizing monomer of formula (VII), W is a halogenated or non-halogenated, aromatic or non-aromatic $C_{2-50}$ hydroxyl-containing organic group having a pKa of less than or equal to 12. In the photoacid generating monomer of formula (VIII), Q is ester-containing or non-ester containing and fluorinated or non-fluorinated and is $C_{1-20}$ alkyl, $C_{3-20}$ cycloalkyl, $C_{6-20}$ aryl, or $C_{7-20}$ aralkyl group, A is ester-containing or non-ester-containing and fluorinated or non-fluorinated, and is $C_{1-20}$ alkyl, $C_{3-20}$ cycloalkyl, $C_{6-20}$ aryl, or $C_{7-20}$ aralkyl, $Z^-$ is an anionic moiety comprising carboxylate, sulfonate, an anion of a sulfonamide, or an anion of a sulfonimide, and $G^+$ is a sulfonium or iodonium cation.

Exemplary acid-deprotectable monomers include but are not limited to:

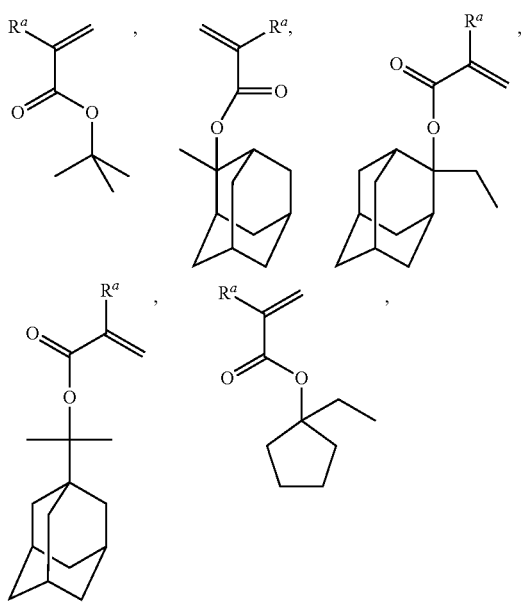

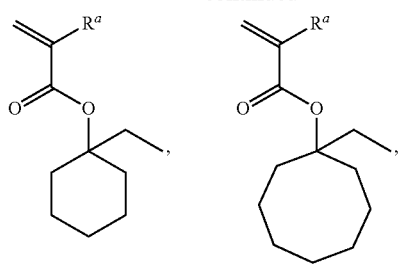

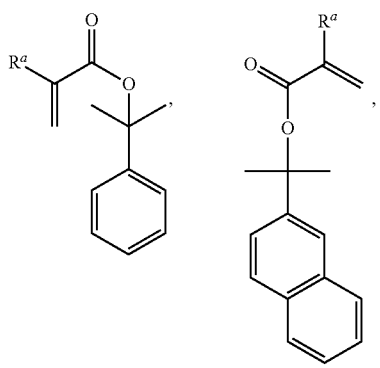

or a combination comprising at least one of the foregoing, wherein $R^a$ is H, F, —CN, $C_{1-6}$ alkyl, or $C_{1-6}$ fluoroalkyl.

Suitable lactone monomers may be of the following formula (IX):

(IX)

wherein $R^a$ is H, F, —CN, $C_{1-6}$ alkyl, or $C_{1-6}$ fluoroalkyl, R is a $C_{1-10}$ alkyl, cycloalkyl, or heterocycloalkyl, and w is an integer of 0 to 5. In formula (IX), R is attached directly to the lactone ring or commonly attached to the lactone ring and/or one or more R groups, and the ester moiety is attached to the lactone ring directly, or indirectly through R.

Exemplary lactone-containing monomers include:

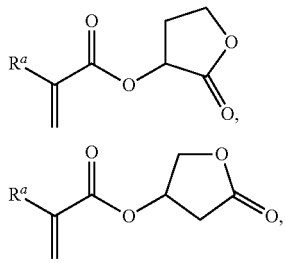

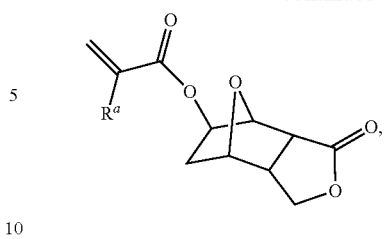

or a combination comprising at least one of the foregoing monomers, wherein $R^a$ is H, F, —CN, $C_{1-10}$ alkyl, or $C_{1-10}$ fluoroalkyl.

Suitable base-soluble monomers may be of the following formula (X):

(X)

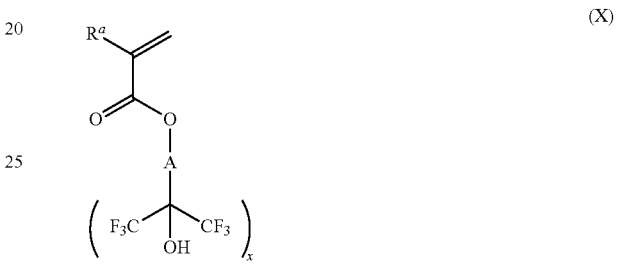

wherein each $R^a$ is independently H, F, —CN, $C_{1-10}$ alkyl, or $C_{1-10}$ fluoroalkyl, A is a hydroxyl-containing or non-hydroxyl containing, ester-containing or non ester-containing, fluorinated or non-fluorinated $C_{1-20}$ alkylene, $C_{3-20}$ cycloalkylene, $C_{6-20}$ arylene, or $C_{7-20}$ aralkylene, and x is an integer of from 0 to 4, wherein when x is 0, A is a hydroxyl-containing $C_{6-20}$ arylene.

Exemplary base soluble monomers include those having the following structures:

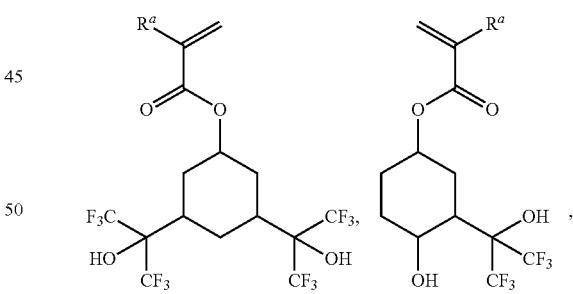

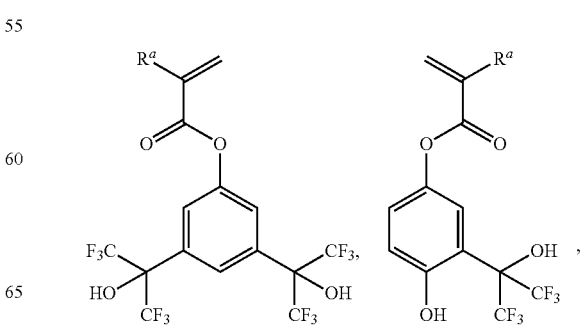

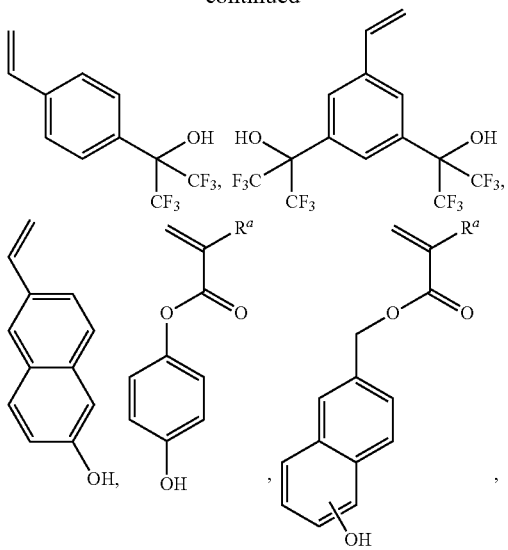

or a combination comprising at least one of the foregoing, wherein $R^a$ is H, F, —CN, $C_{1-6}$ alkyl, or $C_{1-6}$ fluoroalkyl.

Preferred photoacid generating monomer include those of the formulae (XI) or (XII):

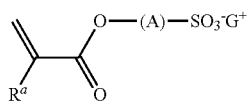
(XI)

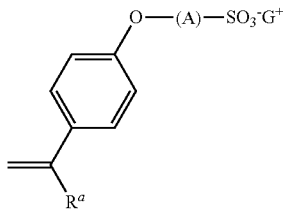
(XII)

wherein each $R^a$ is independently H, F, —CN, $C_{1-6}$ alkyl, or $C_{1-6}$ fluoroalkyl, A is a fluorine-substituted $C_{1-30}$ alkylene group, a fluorine-substituted $C_{3-30}$ cycloalkylene group, a fluorine-substituted $C_{6-30}$ arylene group, or a fluorine-substituted $C_{7-30}$ alkylene-arylene group, and $G^+$ is a sulfonium or iodonium cation.

Preferably, in formulas (XI) and (XII), A is a —[(C($R^1$)$_2$)$_x$(C(=O)O]$_b$—C(($R^2$)$_2$)$_y$(CF$_2$)$_z$— group, or an O—, m- or p-substituted —C$_6$F$_4$— group, where each $R^1$ and $R^2$ are each independently H, F, —CN, $C_{1-6}$ fluoroalkyl, or $C_{1-6}$ alkyl, b is 0 or 1, x is an integer of 1 to 10, y and z are independently integers of from 0 to 10, and the sum of y+z is at least 1.

Exemplary preferred photoacid generating monomers include:

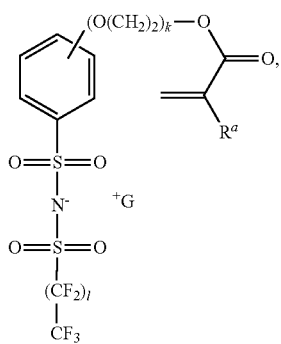

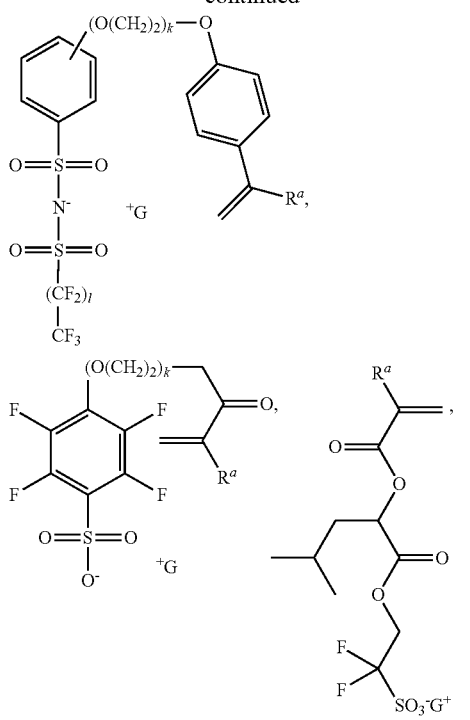

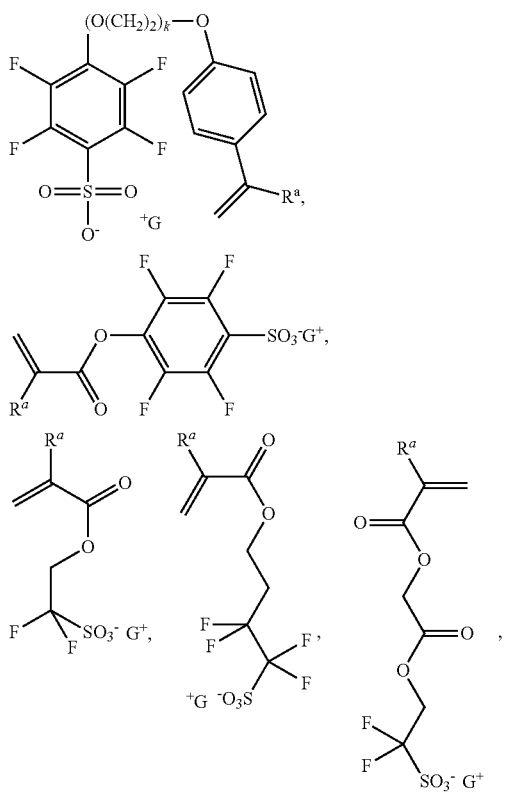

or a combination comprising at least one of the foregoing, where each $R^a$ is independently H, F, —CN, $C_{1-6}$ alkyl, or $C_{1-6}$ fluoroalkyl, k is suitably an integer of from 0 to 5; and $G^+$ is a sulfonium or iodonium cation. $G^+$ as referred to herein throughout the various formulae may be an acid generator as disclosed herein and comprise an oxo-dioxolan moiety and/or an oxo-dioxane moiety.

Preferred photoacid-generating monomers may include sulfonium or iodonium cation. Preferably, in formula (IV), G⁺ is of the formula (XIII):

(XIII)

wherein X is S or I, each R⁰ is halogenated or non-halogenated and is independently $C_{1-30}$ alkyl group; a polycyclic or monocyclic $C_{3-30}$ cycloalkyl group; a polycyclic or monocyclic $C_{4-30}$ aryl group; or a combination comprising at least one of the foregoing, wherein when X is S, one of the R⁰ groups is optionally attached to one adjacent R⁰ group by a single bond, and a is 2 or 3, wherein when X is I, a is 2, or when X is S, a is 3.

Exemplary acid generating monomers include those having the formulas:

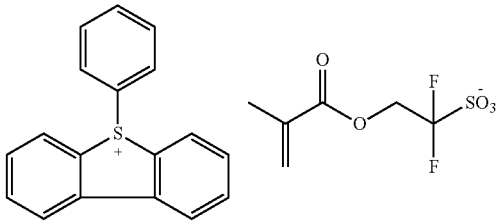

-continued

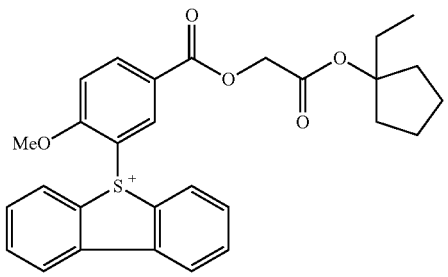

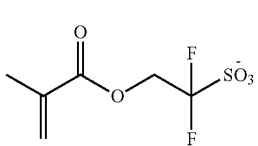

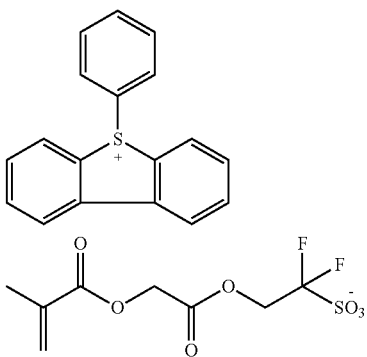

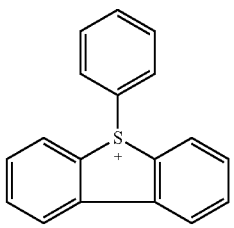

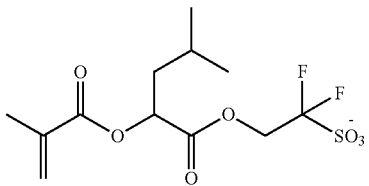

-continued

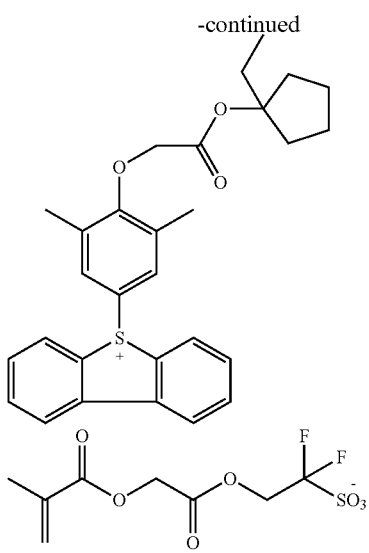

Specifically suitable polymers that have acid-labile deblocking groups for use in a positive-acting chemically-amplified photoresist of the invention have been disclosed in European Patent Application 0829766A2 (polymers with acetal and ketal polymers) and European Patent Application EP0783136A2 (terpolymers and other copolymers including units of 1) styrene; 2) hydroxystyrene; and 3) acid labile groups, particularly alkyl acrylate acid labile groups.

Polymers for use in photoresists of the invention may suitably vary widely in molecular weight and polydisperity. Suitable polymers include those that have an $M_w$ of from about 1,000 to about 50,000, more typically about 2,000 to about 30,000 with a molecular weight distribution of about 3 or less, more typically a molecular weight distribution of about 2 or less.

Preferred negative-acting compositions of the invention comprise a mixture of materials that will cure, crosslink or harden upon exposure to acid, and two or more photoacid generators as disclosed herein. Preferred negative acting compositions comprise a polymer binder such as a phenolic or non-aromatic polymer, a crosslinker component and a photoactive component of the invention. Such compositions and the use thereof have been disclosed in European Patent Applications 0164248 and U.S. Pat. No. 5,128,232 to Thackeray et al. Preferred phenolic polymers for use as the polymer binder component include novolaks and poly(vinylphenol)s such as those discussed above. Preferred crosslinkers include amine-based materials, including melamine, glycolurils, benzoguanamine-based materials and urea-based materials. Melamine-formaldehyde polymers are often particularly suitable. Such crosslinkers are commercially available, e.g. the melamine polymers, glycoluril polymers, urea-based polymer and benzoguanamine polymers, such as those sold by Cytec under tradenames Cymel 301, 303, 1170, 1171, 1172, 1123 and 1125 and Beetle 60, 65 and 80.

Photoresists of the invention also may contain other materials. For example, other optional additives include actinic and contrast dyes, anti-striation agents, plasticizers, speed enhancers and sensitizers. Such optional additives typically will be present in minor concentration in a photoresist composition.

Alternatively, or in addition, other additives may include quenchers that are non-photo-destroyable bases, such as, for example, those based on hydroxides, carboxylates, amines, imines, and amides. Preferably, such quenchers include $C_{1-30}$ organic amines, imines, or amides, or may be a $C_{1-30}$ quaternary ammonium salt of a strong base (e.g., a hydroxide or alkoxide) or a weak base (e.g., a carboxylate). Exemplary quenchers include amines such as tripropylamine, dodecylamine, tris(2-hydroxypropyl)amine, oltetrakis(2-hydroxypropyl)ethylenediamine; aryl amines such as diphenylamine, triphenylamine, aminophenol, and 2-(4-aminophenyl)-2-(4-hydroxyphenyl)propane, Troger's base, a hindered amine such as diazabicycloundecene (DBU) or diazabicyclononene (DBN), or ionic quenchers including quaternary alkyl ammonium salts such as tetrabutylammonium hydroxide (TBAH) or tetrabutylammonium lactate.

Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

The photoresist further includes a solvent generally suitable for dissolving, dispensing, and coating the components used in a photoresists. Exemplary solvents include anisole, alcohols including ethyl lactate, 1-methoxy-2-propanol, and 1-ethoxy-2 propanol, esters including n-butylacetate, 1-methoxy-2-propyl acetate, methoxyethoxypropionate, ethoxyethoxypropionate, ketones including cyclohexanone and 2-heptanone, and a combination comprising at least one of the foregoing solvents.

Such photoresists may include the polymer in an amount of 50 to 99 wt %, specifically 55 to 95 wt %, more specifically 60 to 90 wt %, and still more specifically 65 to 90 based on the total weight of solids. The photo-destroyable base may be present in the photoresist in an amount of 0.01 to 5 wt %, specifically 0.1 to 4 wt %, and still more specifically 0.2 to 3 wt %, based on the total weight of solids. A surfactant may be included in an amount of 0.01 to 5 wt %, specifically 0.1 to 4 wt %, and still more specifically 0.2 to 3 wt %, based on the total weight of solids. A quencher may be included in relatively small amounts of for example, from 0.03 to 5 wt % based on the total weight of solids. Other additives may be included in amounts of less than or equal to 50 wt %, specifically less than or equal to 35%, or more specifically less than or equal to 25%, based on the total weight of solids. The total solids content for the photoresist composition may be 0.5 to 50 wt %, specifically 1 to 45 wt %, more specifically 2 to 40 wt %, and still more specifically 5 to 30 wt %, based on the total weight of solids and solvent. The acid generators should be present in an amount sufficient to enable generation of a latent image in a coating layer of the resist. More specifically, the two or more acid generators will suitably be present in an amount of from about 1 to 50 weight percent of total solids of a resist. It will be understood that the solids includes polymer, quencher, surfactant, and any optional additives, exclusive of solvent.

A coated substrate may be formed from the photoresist containing acid generators which should be present in an amount sufficient to enable generation of a latent image in a coating layer of the resist and acid generators. Such a coated substrate includes: (a) a substrate having one or more layers to be patterned on a surface thereof; and (b) a layer of the photoresist composition including the acid generator over the one or more layers to be patterned. For EUV or e-beam imaging, photoresists may suitably have relatively higher content of acid generator compounds, e.g. where the one or more acid generators comprise 5 to 10 to about 65 weight percent of total solids of the resist. Typically, lesser amounts of the photoactive component will be suitable for chemically amplified resists.

The photoresists of the invention are generally prepared following known procedures with the exception that one or more acid generator compounds of the invention are substituted for prior photoactive compounds used in the formulation of such photoresists. The photoresists of the invention can be used in accordance with known procedures.

Substrates may be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. Preferably, the surfaces of substrates herein include critical dimension layers to be patterned including, for example, one or more gate-level layers or other critical dimension layer on the substrates for semiconductor manufacture. Such substrates may preferably include silicon, SOL strained silicon, and other such substrate materials, formed as circular wafers having dimensions such as, for example, 20 cm, 30 cm, or larger in diameter, or other dimensions useful for wafer fabrication production.

Further, a method of forming an electronic device includes (a) applying a layer of a photoresist composition including on a surface of the substrate; (b) patternwise exposing the photoresist composition layer to activating radiation; and (c) developing the exposed photoresist composition layer to provide a resist relief image.

Applying may be accomplished by any suitable method, including spin coating, spray coating, dip coating, doctor blading, or the like. Applying the layer of photoresist is preferably accomplished by spin-coating the photoresist in solvent using a coating track, in which the photoresist is dispensed on a spinning wafer. During dispense, the wafer may be spun at a speed of up to 4,000 rpm, preferably from about 500 to 3,000 rpm, and more preferably 1,000 to 2,500 rpm. The coated wafer is spun to remove solvent, and baked on a hot plate to remove residual solvent and free volume from the film to make it uniformly dense.

Patternwise exposure is then carried out using an exposure tool such as a stepper, in which the film is irradiated through a pattern mask and thereby is exposed pattern-wise. The method preferably uses advanced exposure tools generating activating radiation at wavelengths capable of high resolution including extreme-ultraviolet (EUV) or e-beam radiation. It will be appreciated that exposure using the activating radiation decomposes the PAG in the exposed areas and generates acid and decomposition by-products, and that the acid then effects a chemical change in the polymer (deblocking the acid sensitive group to generate a base-soluble group, or alternatively, catalyzing a cross-linking reaction in the exposed areas). The resolution of such exposure tools may be less than 30 nm.

Developing the exposed photoresist layer is then accomplished by treating the exposed layer to a suitable developer capable of selectively removing the exposed portions of the film (where the photoresist is positive tone) or removing the unexposed portions of the film (where the photoresist is crosslinkable in the exposed regions, i.e., negative tone). Preferably, the photoresist is positive tone based on a polymer having acid sensitive (deprotectable) groups, and the developer is preferably a metal-ion free tetraalkylammonium hydroxide solution, such as, for example, aqueous 0.26 N tetramethylammonium hydroxide. A pattern forms by developing.

Additionally, for positive resists, unexposed regions can be selectively removed by treatment with a suitable nonpolar solvent for negative tone development. See U.S. 2011/0294069 for suitable procedures for negative tone development of positive photoresists. Typical nonpolar solvents for negative tone development are organic developers, such as a solvent chosen from ketones, esters, hydrocarbons, and mixtures thereof, e.g. acetone, 2-hexanone, methyl acetate, butyl acetate, and tetrahydrofuran.

The photoresist may, when used in one or more such a pattern-forming processes, be used to fabricate electronic and optoelectronic devices such as memory devices, processor chips (CPU's), graphics chips, and other such devices.

EXAMPLE 1

Synthesis of PAG-A1

Photoacid generator PAG-A1 was prepared by the multi-step synthesis as follows.

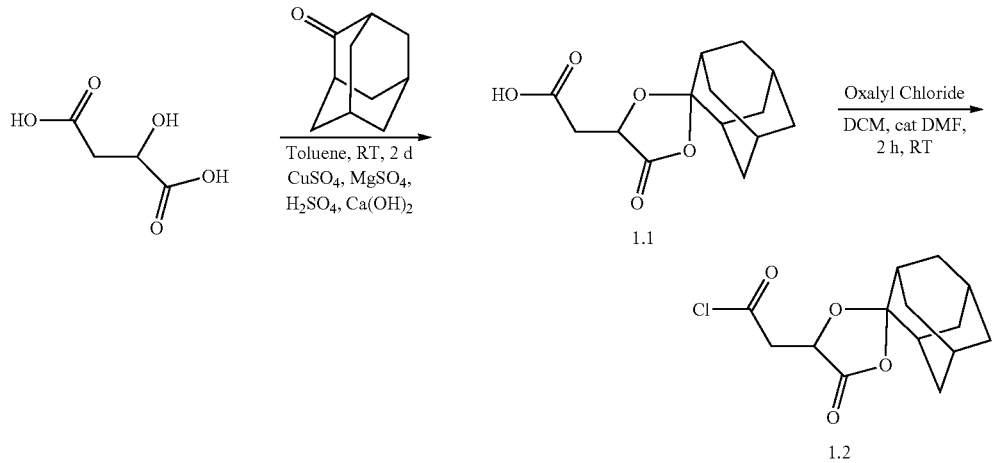

Scheme 1:

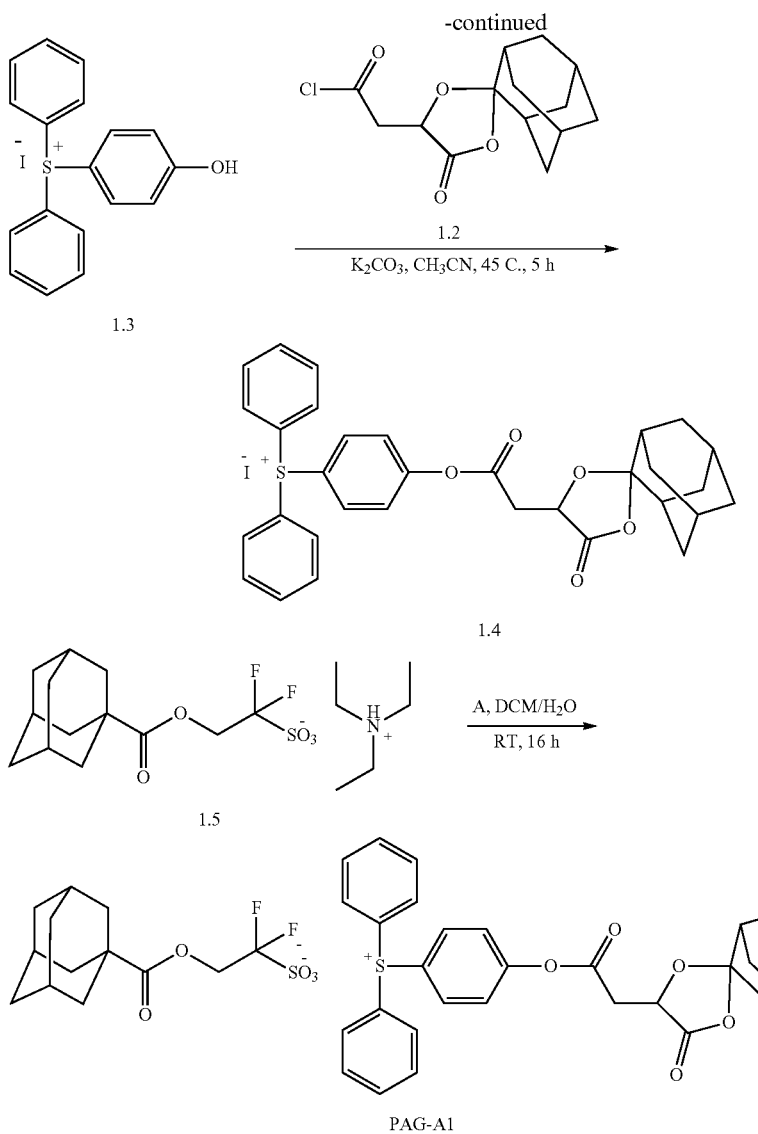

2-(2,2-Adamantyl-5-oxo-1,3-dioxolan-4-yl)acetic acid (1.1): Malic acid (67 g, 0.5 mol), adamantanone (56 g, 0.37 g), copper sulfate (56 g, 0.35 mol), magnesium sulfate (45 g, 0.37 mol) were dissolved in toluene (500 mL). Reaction mixture stirred at 0 C. Conc sulfuric acid (0.5 mL, 0.012 mol) was added dropwise and reaction mixture was stirred at room temp for 48 h. Reaction mixture was filtered through celite pad and washed with acetone (2×200 mL). Calcium hydroxide (11.88 g, 0.16 mol) was added to the filtrate and stirred for one hour at room temp. Reaction mixture was filtered through celite pad and washed with acetone (2×200 mL). The filtrate was evaporated, redissolved in dichloromethane and washed with water (3×200 mL). Evaporate organic phase to get white solids which were washed with heptanes (2×100 mL) to get pure product 1.1 in 81% yield (80 g). $^1$H NMR ((CD$_3$)$_2$CO, 300 MHz): δ 1.70 (m, 6H), 1.94 (m, 8H), 2.80 (m, 2H), 4.73 (t, 1H), 11.00 (bs, 1H).

To a solution of 2-(2,2-adamantyl-5-oxo-1,3-dioxolan-4-yl)acetic acid (1.1, 50 g, 0.19 mol) in dichloromethane (350 mL) was added 1 mL of N,N-dimethylformamide. Oxalyl chloride (35 mL, 0.38 mol) was added dropwise and resulting reaction mixture was stirred at room temp for 2 h. Upon completion of the reaction, solvent was evaporated under reduced pressure to afford white solids as product (1.2) which was used without any further purification. $^1$H NMR ((CD$_3$)$_2$CO, 300 MHz): δ 1.76 (m, 6H), 1.99 (m, 8H), 3.65 (m, 2H), 4.88 (t, 1H).

4-Hydroxyphenyldiphenylsulfonium iodide (1.3, 15 g, 0.037 mol) was dissolved in acetonitrile (200 mL). After complete dissolution, potassium carbonate (24 g, 0.174 mol) was added followed by 2-(2,2-adamantyl-5-oxo-1,3-dioxolan-4-yl)acetyl chloride (1.2, 30 g, 0.105 mol). Reaction mixture was heated at 45° C. for 24 h. Upon cooling, the solids were filtered. Filtrate was evaporated, redissolved in dichloromethane (200 mL), washed with water (2×100 mL), passed through silica gel plug eluting with dichloromethane:acetone (1.5:1). Evaporate solvent under reduced pressure and precipitate in MTBE to get off white solids as product (1.4) in 75% yield (18 g). $^1$H NMR (CDCl$_3$, 300 MHz): δ 1.70 (m, 8H), 2.00 (m, 6H), 3.18 (m, 2H), 4.81 (t, 1H), 7.50 (d, 2H), 7.73 (m, 10H), 7.84 (d, 2H). In the next step, triethylammonium 2-(adamantane-1-carbonyloxy)-1,1-difluoroethanesulfonate (1.5, 30 g, 0.07 mol) and (4-(2-(2,2-Adamantyl-5-oxo-1,3-dioxolan-4-yl)acetoxy)phenyl)diphenylsulfonium iodide (1.4, 45 g, 0.068 mol) were dissolved in 500 mL DCM and 500 mL deionized water. The reaction mixture was rapidly stirred at room temp for 16 h. Organic layer was separated and washed seven times with 300 mL volumes of Millipore deionized water. The combined filtrate was evaporated to yield crude product which was redissolved in dichloromethane (120 mL) and poured slowly through syringe filter into 2 L rapidly stirred methyl tert-butyl ether (MTBE). The white suspension was stirred 1 h, let stand for 30 min, MTBE was decanted and white solids were dried under high vacuum to yield 40 g (68% yield) of PAG-A1. $^1$H NMR (CDCl$_3$, 300 MHz): δ 1.68 (m, 12H), 1.97 (m, 17H), 3.17 (m, 2H), 4.74 (t, 2H), 4.80 (m, 1H), 7.48 (d, 2H), 7.73 (m, 10H), 7.83 (d, 2H). $^{19}$F NMR: δ −114.5.

EXAMPLE 2

Synthesis of PAG-2B

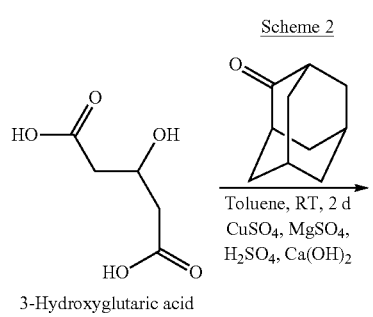

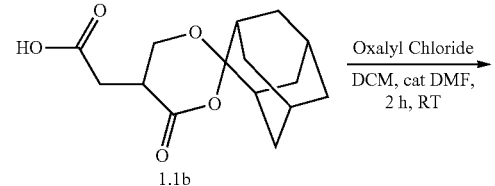

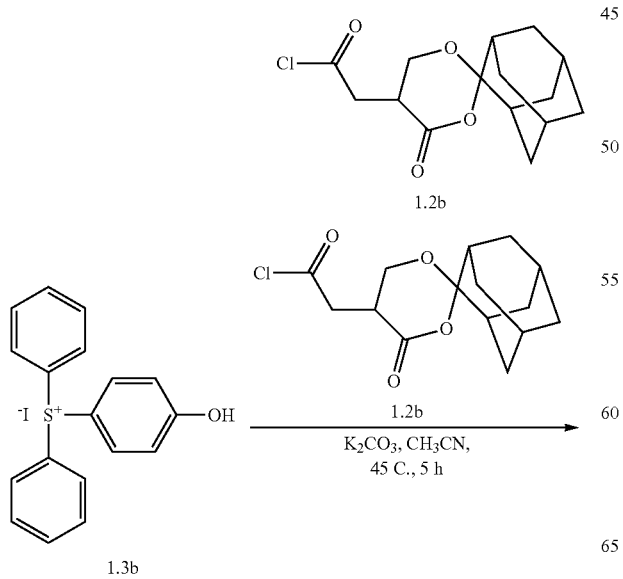

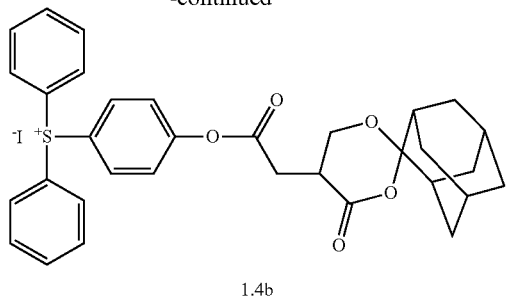

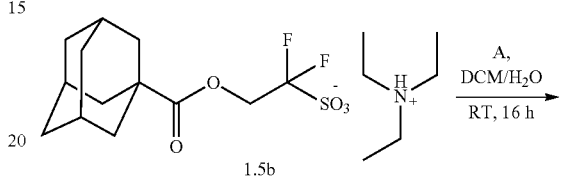

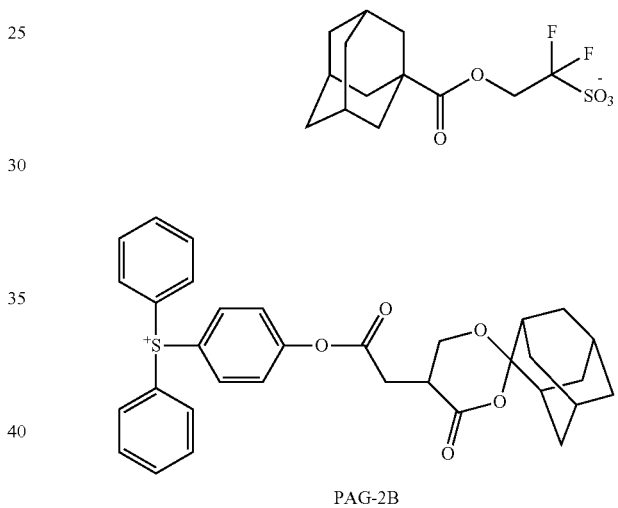

The title acid generator PAG-2B is prepared as set forth in the above scheme starting from 3-hydroxyglutaric acid.

EXAMPLE 3

Synthesis of PAG-A2

Photoacid generator PAG-A2 was prepared by a multi-step synthesis as follows.

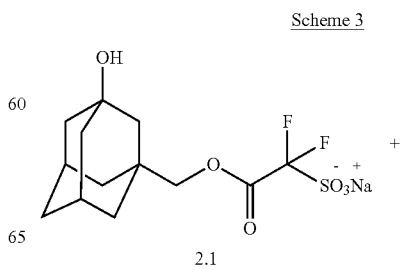

37

-continued

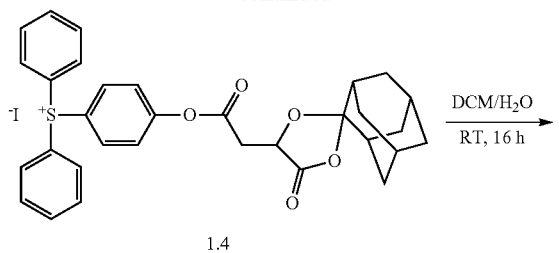

1.4

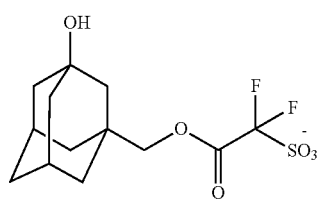

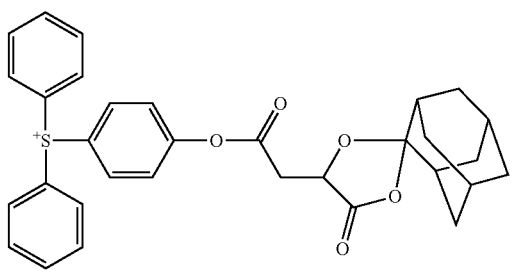

PAG-A2

4-(2-(2,2-Adamantyl-5-oxo-1,3-dioxolan-4-yl)acetoxy) phenyl)diphenylsulfonium iodide (1.4, 10 g, 15.27 mmol) and sodium 1,1-difluoro-2-((-3-hydroxyadamantan-1-yl) methoxy)-2-oxoethanesulfonate (AdOH CDFMSNa) (2.1, 5.52 g, 15.22 mmol) were dissolved in 150 mL dichloromethane and 150 mL deionized water and stirred at room temp for 16 h under nitrogen. The reaction was stopped and organic layer was separated and washed five times with 150 mL volumes of Millipore deionized water. The combined filtrate was evaporated to yield crude product which was redissolved in dichloromethane (120 mL) and poured slowly through syringe filter into 2 L rapidly stirred methyl tert-butyl ether (MTBE) to produce 8 g (60.6% yield) of PAG-A2. $^1$H NMR (CDCl$_3$, 300 MHz): δ 1.68 (m, 12H), 1.97 (m, 17H), 3.20 (m, 2H), 3.82 (s, 2H), 4.94 (t, 1H), 7.60 (d, 2H), 7.86 (m, 10H), 7.98 (d, 2H). $^{19}$F NMR: δ −110.2.

EXAMPLE 4

Synthesis of PAG-A3

Photoacid generator PAG-A3 was prepared as follows.

Scheme 4

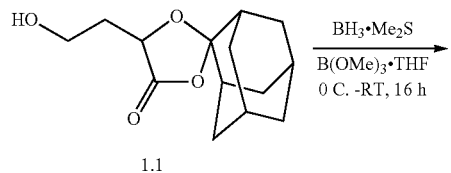

38

-continued 5-(2-Hydroxyethyl)-2,2-adamantyl-1,3-dioxolan-4-one (3.1): A solution of 2-(2,2-adamantyl-5-oxo-1,3-dioxolan-4-yl)acetic acid (1.1, 24 g, 0.09 mol) in anhyd. tetrahydrofuran (100 mL) was cooled to 0° C. To the cold solution, BH$_3$.Me$_2$S (2M in THF, 91 mL, 0.18 mol) was added dropwise followed by dropwise addition of trimethoxyborate (20.3 mL, 0.18 mol). The resulting reaction mixture was slowly warmed to room temp and stirred for 2 days. Upon completion of the reaction, reaction mixture was cooled to 0 C. Slowly add the methanol (~100 mL) to quench the reaction which evolves exothermic reaction. Solvent was evaporated under reduced pressure to yield the product (3.1) as thick oil which was used without any further purification.

2-(2,2-Adamantyl-5-oxo-1,3-dioxolan-4-yl)ethyl 2-chloroacetate (3.2): To a mixture of 5-(2-hydroxyethyl)-2,2-adamantyl-1,3-dioxolan-4-one (3.1, 36 g, 0.144 mol) and triethylamine (29 g, 0.29 mol) in dichloromethane (500 mL) at 0° C. was add slowly chloroacetyl chloride (19.5 g, 0.17 mol). The mixture was stirred at room temperature for 24 h, filtered and the organic solution was washed water twice. Purification by short plug of silica gel produced pure product (3.2) as pale viscous oil in 64% yield (30 g). $^1$H NMR ((CD$_3$)$_2$CO, 300 MHz): δ 1.75 (m, 6H), 1.99 (m, 8H), 2.82 (m, 2H), 3.67 (m, 1H), 4.60 (t, 2H), 4.34 (s, 2H).

(4-(2-(2-(2,2-Adamantyl--5-oxo-1,3-dioxolan-4-yl)ethoxy)-2-oxoethoxy)phenyl)diphenylsulfonium Iodide (3.3): 4-Hydroxyphenyldiphenylsulfonium iodide (1.3, 20 g, 0.056 mol) was dissolved in acetonitrile (300 mL). After complete dissolution, potassium carbonate (35 g, 0.25 mol) was added followed by 2-(2,2-Adamantyl-5-oxo-1,3-dioxolan-4-yl)ethyl 2-chloroacetate (3.2, 20 g, 0.062 mol). Reaction mixture was heated at 45° C. for 24 h. Upon cooling, the solids were filtered. Filtrate was evaporated, redissolved in dichloromethane (200 mL), washed with water (2×100 mL), passed through silica gel plug eluting with dichloromethane: acetone (1.5:1). Evaporate solvent under reduced pressure and precipitate in MTBE to get off white solids as product (1.4) in 69% yield (27 g).

(PAG-A3): In a 2 L round bottom flask triethylammonium 2-(adamantane-1-carbonyloxy)-1,1-difluoroethane-sulfonate) (1.5, 10 g, 0.024 mol) and (4-(2-(2-(2,2-adamantyl-5-oxo-1,3-dioxolan-4-yl)ethoxy)-2-oxoethoxy)phenyl) diphenylsulfonium Iodide (3.3, 16.8 g, 0.024 mol) were dissolved in 500 mL DCM and 500 mL deionized water. The reaction mixture was rapidly stirred at room temp for 16 h under nitrogen. Organic layer was separated and washed seven times with 300 mL volumes of Millipore deionized water. The combined filtrate was evaporated to yield crude product which was redissolved in dichloromethane (120 mL) and poured slowly into 2 L rapidly stirred methyl tert-butyl ether (MTBE) followed by isolation of the product. Yield of APG-A3 was 16 g (75% yield) of PAG-A3. $^1$H NMR ((CD$_3$)$_2$CO, 300 MHz): δ 1.68 (m, 12H), 1.99 (m, 17H), 4.16 (m, 1H), 4.38 (t, 2H), 4.59 (m, 2H), 4.91 (s, 2H), 2.08 (m, 2H), 7.38 (d, 2H), 7.84 (m, 12H). $^{19}$F NMR: $^{19}$F NMR: δ –116.21.

EXAMPLE 5

Synthesis of PAG-A4

Photoacid generator PAG-A4 was prepared by the multi-step synthesis detailed in Scheme 5 and the following paragraphs.

Scheme 5:

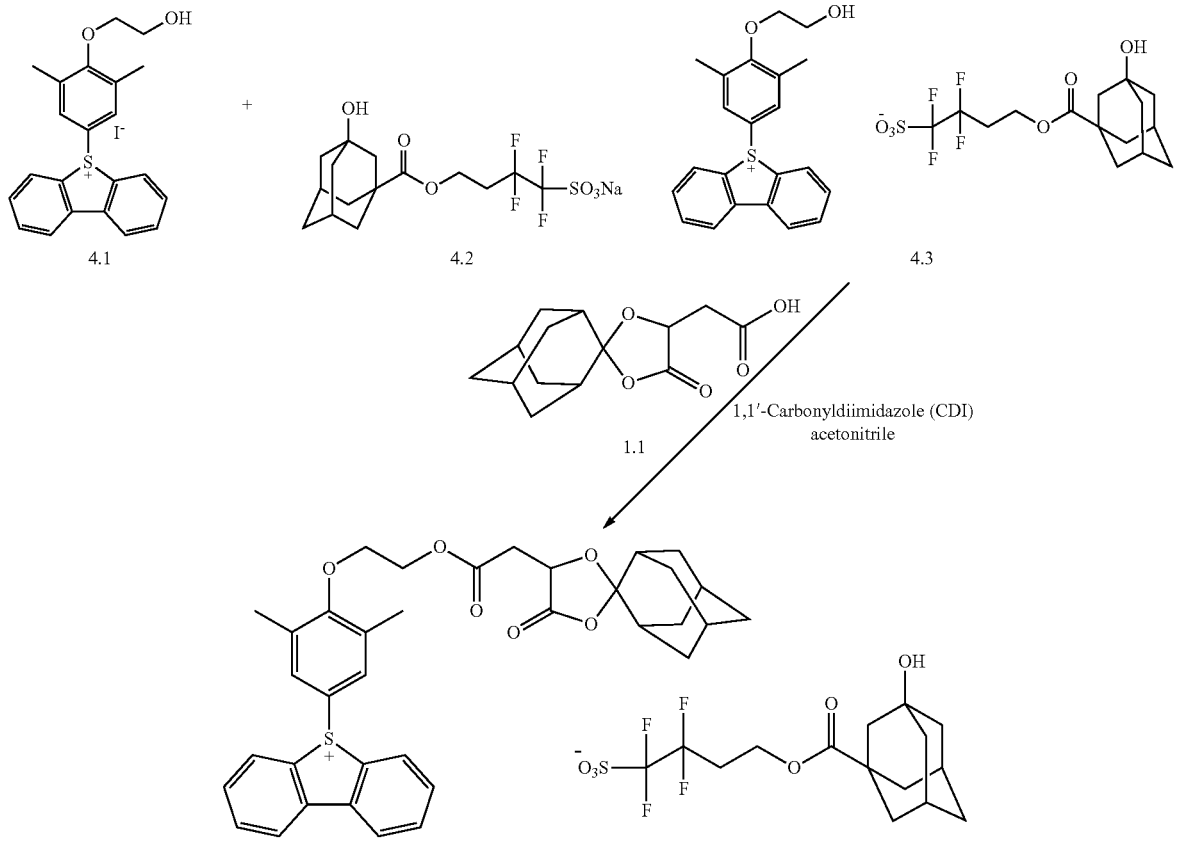

A mixture of salt 4.1 (2.0, 4.20 mmol) and salt 4.2 (1.96 g, 4.60 mmol) in 20 mL of $CH_2Cl_2$ and 20 mL of water was stirred at room temperature for 6 h. The organic phase was separated, washed with deionized water (5×20 mL), concentrated to ⅓ of the initial volume and poured slowly into 75 mL methyl t-butyl ether to precipitate the product 4.3. Product 4.3 was filtered dried and used in the next step.

To a suspension of compound 1.1 (1.5 g, 5.6 mmol) in 20 ml of tetrahydrofuran (THF) was added 1,1'-Carbonyldiimidazole (0.9 g, 5.55 mmol). The mixture was stirred at room temperature for 2 hours. The reaction temperature was raised to 70° C. followed by the addition of compound 4.3 (3.0 g, 3.98 mmol). The mixture was stirred at 70° C. for 16 h, and then cooled to room temperature. The solvent was fully removed under reduced pressure and the resulting residue was dissolved in 20 dichloromethane. The resulting solution was washed excessively with deionized water, concentrated to ⅓ of the initial volume and poured into large excess of methyl t-butyl ether. Product PAG-A4 was filtered and dried. The yield from the second step was 2.3 g (58%).

EXAMPLE 6

Lithographic Evaluation

The photoacid generators were evaluated lithographically according to the following procedure. Photoresists were formulated using the components and proportions shown in Table 2. The commercial photoresist polymer A2 was used in all examples. Polymer A2 is a pentapolymer incorporating monomers M1, M2, M3, M4 and M5, where the mole percentage of M1/M2/M3/M4/M5 is 20/20/30/20/10 for a total of 100 mole percent of monomers. The MW of the polymer was 8,000 g/mol. Note that the PAG (see Table 2), base (t-butyloxycarbonyl-4-hydroxypyridine, TBOC-4HP), and surface leveling agent (surfactant) PF 656, available from Omnova, are in weight percent based on 100% solids content, with the balance of the solids being the polymer. The solvents used in these formulations are PGMEA (S1) and HBM (S2). The final % solids in both examples were 4 wt %. The weight ratio of solvent S1:S2 in the final formulation was 1:1. Structures of the comparative PAGs are shown in Table 1.

TABLE 1

| PAG | PAG Name | Structure of the PAG |
|---|---|---|
| Comparative PAG 1 | Triphenylsulfonium 2-(adamantane-1-carbonyloxy)-1,1-difluoroethane sulfonate | |
| Comparative PAG 2 | Triphenylsulfonium perfluorobutane-sulfonate | |

Photoresist formulation compositions for Comparative Example and Examples 1 and 2 are shown in Table 2 below:

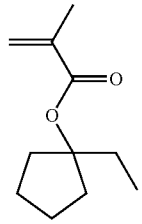

M1

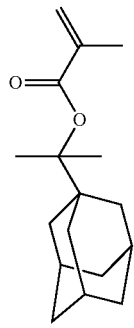

M2

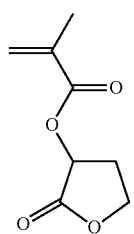

M3

-continued

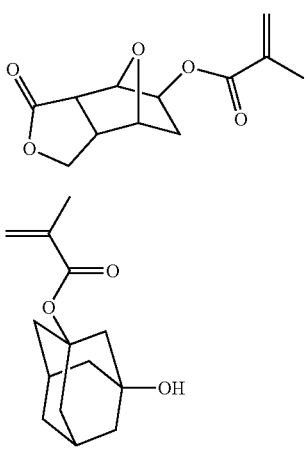

M4

M5

TABLE 2

| Sample | PAG | PAG (wt %) | Base (wt %) | SLA (wt %) |
|---|---|---|---|---|
| Comparative Example 1 | Comparative PAG 1 | 11.38 | 1.03 | 0.1 |
| Comparative Example 2 | Comparative PAG 2 | 10.91 | 1.03 | 0.1 |
| Example 1 | PAG-A1 | 15.40 | 1.03 | 0.1 |

The above photoresists were lithographically processed as follows. The photoresist was spin coated onto a 200 mm silicon wafer having 84 nm of an organic antireflective coating (AR™77, Dow Electronic Materials) and baked at 110° C. for 60 seconds, to form a resist film 100 nm in thickness. The photoresist was exposed with ArF excimer laser (193 nm) through a mask pattern targeting a line and space pattern (L/S pattern) having a line width of 90 nm and a pitch of 180 nm, using an ArF exposure apparatus ASML-1100 (manufactured by ASML), NA (numerical aperture)=0.75 under annular illumination with outer/inner sigma of 0.89/0.64 with focus offset/step 0.10/0.05. The wafers were post exposure baked (PEB) at 100° C. for 60 seconds followed by developing with 0.26 N aqueous tetramethylammonium hydroxide (TMAH) developer and subsequent water wash.

In each example, a L/S pattern having a line width of 90 nm and a pitch of 180 nm was formed. Mask Error Factor (MEF) and Exposure Latitude (EL) were determined by processing the image captured by top-down scanning electron microscopy (SEM) using a Hitachi 9380 CD-SEM, operating at an accelerating voltage of 800 volts (V), probe current of 8.0 picoamperes (pA), using 200 Kx magnification. Exposure latitude (EL) was defined as a difference in exposure energy to print +/−10% of the target diameter normalized by the sizing energy. Mask Error Factor (MEF) was defined as the ratio of CD change on the resolved resist pattern to the relative dimension change on the mask pattern.

The results from the lithographic evaluation of the above photoresist formulations are reported in Table 3.

TABLE 3

| PAG | Eo | EL % | MEF | LWR |
|---|---|---|---|---|
| Comparative PAG 1 | 7.4 | 12.14 | 3.31 | 13.6 |
| Comparative PAG 2 | 5.4 | 9.62 | 4.26 | 12.4 |
| PAG-A1 | 9.8 | 12.51 | 3.14 | 12.2 |

As seen in Table 3, photoresist that comprise PAG-A1 exhibit improved lithographic performance in terms of exposure latitude, and Mask Error Factor and Line wedge roughness (LWR).

EXAMPLE 7

Further Photoresist Preparation

A positive-tone photoresist composition is prepared by combining 55.432 g of a 10 wt % solution of the Polymer A2 as described in Example 6 above in ethyl lactate, 94.235 g of a 2 wt % solution of the acid generator PAG-2B of Example 2 above, 13.304 g of a 0.5 wt % solution of tetrakis(2-hydroxypropyl)ethylenediamine in ethyl lactate, 1.109 g of a 0.5 wt % solution of fluorinated surfactant (Omnova PF656) in ethyl lactate, 48.170 g of ethyl lactate and 87.750 g of 2-hydroxyisobutyric acid methyl ester. The formulated resist was passed through a 0.01 μm PTFE filter. The thus prepared resist is spin coated onto a silicon wafer, soft baked to remove carrier solvent and exposed through a photomask to EUV radiation. The imaged resist layer is then baked at 110° C. for 60 seconds and then developed with an aqueous alkaline composition.

What is claimed is:

1. A photoacid generator comprising a group of the following Formulae I or II:

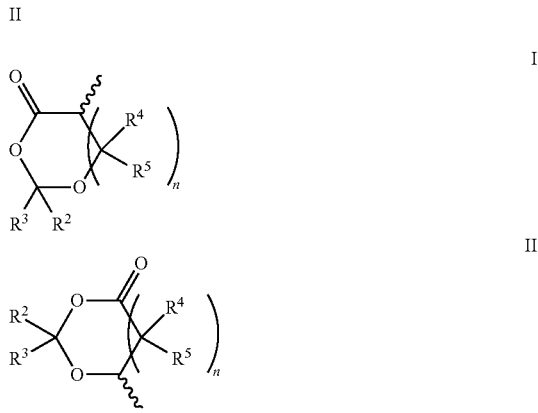

wherein in each of Formulae I and II:
the waved line represents a covalent linkage connecting the depicted moiety to the larger acid generator material;
$R^2$, $R^3$, $R^4$ and $R^5$ are each independently hydrogen or a non-hydrogen substituent, with at least one of $R^2$ and $R^3$ being a non-hydrogen substituent;
$R^2$ and $R^3$ optionally may be taken together to form a ring;
$R^4$ and $R^5$ optionally may be taken together to form a ring; and
$R^4$ and/or $R^5$ optionally may be taken together with the covalent linkage to form a ring; and
n is 0 or 1.

2. The photoacid generator of claim 1 wherein the photoacid generator is an onium compound.

3. The photoacid generator of claim 1 wherein the photoacid generator comprises a cation component that comprises a group of Formula I.

4. The photoacid generator of claim 1 wherein the photoacid generator comprises a group of the following formula (IV):

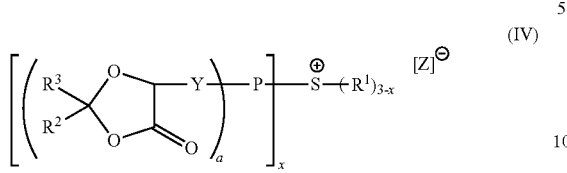

wherein:

x is 1,2 or 3;

a is a positive integer of from 1 to 12;

$R^2$ and $R^3$ are each independently hydrogen, optionally substituted alkyl, optionally substituted heteroalkyl, optionally substituted alicyclic; optionally substituted heteroalicyclic; optionally substituted carbocyclic aryl; or optionally substituted heteroaromatic; $R^2$ and $R^3$ may be taken together to form an aromatic or non-aromatic cyclic group, with at least one of $R^2$ and $R^3$ being a non-hydrogen substituent;

Y is a covalent bond or a linker group;

P is optionally substituted alkyl, optionally substituted heteroalkyl, optionally substituted alicyclic, optionally substituted heteroalicyclic, optionally substituted carbocyclic aryl, optionally substituted heteroaromatic;

each $R^1$ is independently optionally substituted alkyl, optionally substituted heteroalkyl; optionally substituted alicyclic; optionally substituted heteroalicyclic; optionally substituted carbocyclic aryl; or optionally substituted heteroaromatic aryl, when x is 1, two $R^1$ groups and the adjacent sulfur atom optionally may be taken together to form a ring; and Z is a counter anion.

5. The photoacid generator of claim 1 wherein the acid generator comprises a group of Formula I.

6. A photoacid generator of claim 1 wherein the photoacid generator is a component of a resin.

7. A photoresist composition comprising 1) a resin and 2) one or more photoacid generators of claim 1.

8. A method for providing a photoresist relief image, comprising:
   a) applying a coating layer of a photoresist composition of claim 7 on a substrate; and
   b) exposing the photoresist composition layer to activating radiation and developing the exposed photoresist composition coating layer.

9. The method of claim 8 wherein the activating radiation is EUV or electron-beam radiation.

10. The photoacid generator of claim 1 wherein the acid generator comprises a group of Formula II.

11. The photoacid generator of claim 1 wherein the acid generator comprises a group of Formula II.

12. A photoresist composition comprising 1) a resin and 2) one or more photoacid generators of claim 5.

13. A photoresist composition comprising 1) a resin and 2) one or more photoacid generators of claim 10.

14. A method for providing a photoresist relief image, comprising:
   a) applying a coating layer of a photoresist composition of claim 12 on a substrate; and
   b) exposing the photoresist composition layer to activating radiation and developing the exposed photoresist composition coating layer.

15. A method for providing a photoresist relief image, comprising:
   a) applying a coating layer of a photoresist composition of claim 13 on a substrate; and
   b) exposing the photoresist composition layer to activating radiation and developing the exposed photoresist composition coating layer.

16. A photoresist composition comprising a resin and a photoacid generator of the following Formula III:

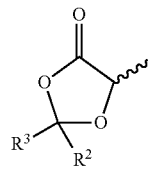

wherein $R^2$ and $R^3$ are each independently hydrogen or non-hydrogen substituent, and $R^2$ and $R^3$ may be optionally taken together to form a ring such as optionally substituted $C_{3-30}$ alicyclic which optionally may have 1, 2, or 3 N, O or S ring members; and the waved line represents a covalent linkage to the photoacid generator.

17. The photoresist composition of claim 16 wherein at least one, or both, of $R^2$ and $R^3$ is a non-hydrogen substituent.

18. A photoresist composition comprising a resin and a photoacid generator of the following Formula V:

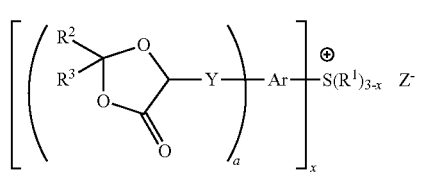

wherein in Formula V:

a is an integer from 1 to 12;

x is an integer from 1 to 3,

Y is a linker;

Ar is an optionally substituted $C_5$ or greater monocyclic, polycyclic, or fused polycyclic cycloalkyl; or an optionally substituted $C_5$ or greater monocyclic, polycyclic, or fused polycyclic aryl group, wherein the cycloalkyl or aryl is a carbocycle (e.g. phenyl, naphthyl, anthracenyl) or comprises a heteroatom comprising O, S, N, F, or a combination comprising at least one of the foregoing, each $R^1$ is independently optionally substituted carbocyclic aryl; optionally substituted heteroaryl; optionally substituted alkyl, a $C_{3-40}$ cycloalkyl, wherein when x is 1, two groups $R^1$ may be optionally taken together to form a ring structure, $R^2$ and $R^3$ independently are hydrogen or a non-hydrogen substituent such as optionally substituted alkyl, optionally substituted heteroalkyl, optionally substituted alicyclic, optionally substituted heteroalicyclic, optionally substituted carbocyclic aryl or optionally substituted heteroaromatic;

$Z^-$ is a non-nucleophilic anion such as carboxylate, sulfate, sulfonate, sulfamate, or the anion of a sulfonamide.

19. A photoresist composition comprising a resin and a photoacid generator of the following Formula VI and VII:

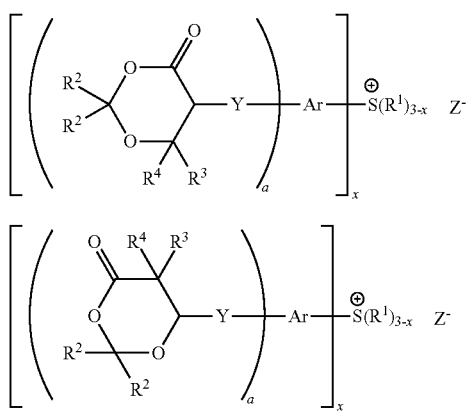

wherein:
a is an integer from 1 to 12;
x is an integer from 1 to 3,
Y is a linker;

Ar is an optionally substituted $C_5$ or greater monocyclic, polycyclic, or fused polycyclic cycloalkyl; or an optionally substituted $C_5$ or greater monocyclic, polycyclic, or fused polycyclic aryl group, wherein the cycloalkyl or aryl is a carbocycle (e.g. phenyl, naphthyl, anthracenyl) or comprises a heteroatom comprising O, S, N, F, or a combination comprising at least one of the foregoing, each $R^1$ is independently optionally substituted carbocyclic aryl; optionally substituted heteroaryl; optionally substituted alkyl, a $C_{3-40}$ cycloalkyl, wherein when x is 1, two groups $R^1$ may be optionally taken together to form a ring structure, each $R^2$ and $R^3$ independently are hydrogen or a non-hydrogen substituent such as optionally substituted alkyl, optionally substituted heteroalkyl, optionally substituted alicyclic, optionally substituted heteroalicyclic, optionally substituted carbocyclic aryl or optionally substituted heteroaromatic;

$R^4$ and/or $R^5$ can optionally covalently attach to Y to form a ring.

20. The photoresist composition of claim 19 comprising a photoacid generator of Formula VI.

21. The photoresist composition of claim 19 comprising a photoacid generator of Formula VII.

* * * * *